US008580943B2

(12) United States Patent
Kirsch et al.

(10) Patent No.: US 8,580,943 B2
(45) Date of Patent: *Nov. 12, 2013

(54) CHIMERIC PROMOTERS CAPABLE OF MEDIATING GENE EXPRESSION IN PLANTS UPON PATHOGEN INFECTION AND USES THEREOF

(75) Inventors: Christoph Kirsch, Cologne (DE); Elke Logemann, Pulheim-Dansweiler (DE); Klaus Hahlbrock, Hinterzarten (DE); Paul Rushton, Brookings, SD (US); Imre Somssich, Cologne (DE)

(73) Assignee: Max-Planck-Gesellschaft zur Foerderung der Wissenschaften e.V., Berlin (DE)

( * ) Notice: Subject to any disclaimer, the term of this patent is extended or adjusted under 35 U.S.C. 154(b) by 10 days.

This patent is subject to a terminal disclaimer.

(21) Appl. No.: 13/225,509

(22) Filed: Sep. 5, 2011

(65) Prior Publication Data

US 2012/0117689 A1 May 10, 2012

Related U.S. Application Data

(63) Continuation-in-part of application No. 09/831,272, filed as application No. PCT/EP99/08710 on Nov. 12, 1999, now Pat. No. 8,013,138.

(30) Foreign Application Priority Data

Nov. 12, 1998 (EP) .................................. 98 12 1160
Aug. 27, 1999 (EP) .................................. 99 11 6981

(51) Int. Cl.
*C12N 15/82* (2006.01)
*C12N 15/10* (2006.01)
*C12N 15/63* (2006.01)

(52) U.S. Cl.
USPC .......... 536/24.1; 435/410; 435/468; 435/419; 800/298

(58) Field of Classification Search
None
See application file for complete search history.

(56) References Cited

U.S. PATENT DOCUMENTS

| 5,689,056 A | 11/1997 | Cramer et al. |
| 5,695,939 A | 12/1997 | Zhu et al. |
| 5,910,629 A | 6/1999 | Strittmatter |
| 5,994,527 A | 11/1999 | Strittmatter et al. |
| 8,013,138 B1 * | 9/2011 | Kirsch et al. ................. 536/24.1 |

FOREIGN PATENT DOCUMENTS

| WO | 9220807 A | 11/1992 |
| WO | 9319188 A | 9/1993 |
| WO | 9503690 A | 2/1995 |
| WO | 9628561 A | 9/1996 |
| WO | 9636697 A | 11/1996 |
| WO | 9803536 A | 1/1998 |

OTHER PUBLICATIONS

Van De Loecht et al "A 125 pb promoter fragment is sufficient for strong elicitor-mediated gene activation in parsley" 1990, the EMBO Journal, 9(9), pp. 2945-2950 XP002364318.
Rushton P J et al. "Interaction of elicitor-induced DNA-binding proteins with elicitor response elements in the promoters of parsley PR1 genes", EMBO Journal, vol. 15, No. 20, 1996, pp. 5690-5700 XP002138284.
Raventos D et al. "A 20 bp cis-acting element is both necessary and sufficient to mediate elicitor response of a maize PRms gene" PLANT JOURNAL, vol. 7, No. 1, Jan. 1995, pp. 147-155 XP002107426.
Ohme-Takagi M and Shinshi H "Ethylene-inducible DNA binding proteins that interact with an ethylene-responsive element". Plant Cell, American Society of Plant Physiologist, Rockville, MD, US, vol. 7, No. 2, Feb. 1, 1995, pp. 173-182, XP002108954, ISSN: 1040-4651, DOI: DOI:10.1105/TPC.7.2.173, p. 177, right-hand column, last paragraph—p. 178, left hand column, paragraph 1; figure 1.
Shinshi H et al: "Identification of an Ethylene-Responsive Region in the Promoter of a Tobacco Glas I Chitinase Gene". Plant Molecular Biology, Springer, Dordrecht, NL, vol. 27, No. 5, Jan. 1, 1995, pp. 923-932 XP001084582, ISSN: 0167-4412, DOI:DOI:10.1007/BF00037020.
Somssich I E et al: "Differential Early Activation of Defense-Related Genes in Elicitor-Treated Parsley Cells". Plant Molecular Biology, Springer, Dordrecht, NL vol. 12, No. 2, Feb. 1, 1989, pp. 227-234, XP000051748, ISSN: 0167-4412, DOI: DOI: 10.1007/BF00020507.
Rushton P J et al: "Synthetic Plant Promoters Containing Defined Regulatory Elements Provide Novel Insights into Pathogen- and Wound-Induced Signaling" The Plant Cell, vol. 14, 749-763, Apr. 2002, 2002 American Society of Plant Biologists.
Kirsch C et al: "A novel regulatory element involved in rapid activation of parsley ELI7 gene family members by fungal elicitor of pathogen infection" Molecular Plant Pathology (2000) 1(4), 243-251, 2000 Blackwell Science LTD.

* cited by examiner

*Primary Examiner* — Maria Marvich
(74) *Attorney, Agent, or Firm* — Patent Central LLC; Stephen A. Pendorf

(57) ABSTRACT

Described are synthetic promoters capable of mediating gene expression in plants upon pathogen infection. Furthermore, recombinant genes and vectors comprising said chimeric promoters as well as host cells transformed with such chimeric promoters, recombinant genes, or vectors are provided. Additionally, diagnostic compositions and kits comprising such chimeric promoters, recombinant genes, vectors or cells are described. Provided are further methods for the identification of compounds being capable of activating or inhibiting genes that are specifically expressed in plants upon pathogen infection employing the above described means. Furthermore, transgenic plant cells, plant tissue, and plants containing the above-described chimeric promoters, recombinant genes, and vectors as well as the use of the aforementioned chimeric promoters, recombinant genes, vectors and/or compounds identified by the method of the invention in plant cell and tissue culture, plant breeding, and/or agriculture are described.

10 Claims, 21 Drawing Sheets

Fig. 1

Restriction map of plasmid ms23

```
                         NlaIV
                   AciI  |
                   HhaI  |
                   ThaI  |
                      |  |
    AGGTGGCACTTTTCGGGGAAATGTGCGCGGAACCCCTATTTGTTTATTTTTCTAAATACA
  1 ---------+---------+---------+---------+---------+---------+ 60
    TCCACCGTGAAAAGCCCCTTTACACGCGCCTTGGGGATAAACAAATAAAAGATTTATGT

NlaIII
               BciVI|
              RcaI  |
           BsmAI |  |
           BsrBI |  |
            AciI|| |                              SspI    EarI
              ||||| |                              |       |
    TTCAAATATGTATCCGCTCATGAGACAATAACCCTGATAAATGCTTCAATAATATTGAAA
 61 ---------+---------+---------+---------+---------+---------+ 120
    AAGTTTATACATAGGCGAGTACTCTGTTATTGGGACTATTTACGAAGTTATTATAACTTT

Fnu4HI
                                                       TauI
              MboII         MslI                       AciI|
                |             |                           ||
    AAGGAAGAGTATGAGTATTCAACATTTCCGTGTCGCCCTTATTCCCTTTTTTGCGGCATT
121 ---------+---------+---------+---------+---------+---------+ 180
    TTCCTTCTCATACTCATAAGTTGTAAAGGCACAGCGGGAATAAGGGAAAAAACGCCGTAA

DpnI
                                    SfaNI              Sau3AI|
              HphI                  TaqII     HphI    TaqII ||
                |                     ||        |        | ||
    TTGCCTTCCTGTTTTTGCTCACCCAGAAACGCTGGTGAAAGTAAAAGATGCTGAAGATCA
181 ---------+---------+---------+---------+---------+---------+ 240
    AACGGAAGGACAAAAACGAGTGGGTCTTTGCGACCACTTTCATTTTCTACGACTTCTAGT

MaeIII
           Eco57I                                         SmlI
           BsiHKAI                                        DpnI
           Bsp1286I                                       BstYI
             BssSI                      BsrI              Sau3AI
             BseSI                      DpnI       AlwI    |
             CviRI                      BstYI      AciI    |
            ApaLI                       Sau3AI     MspA1I  |
           MboII|             TaqI      UbaLI      AlwI    |
              |||              |          |          |    |
    GTTGGGTGCACGAGTGGGTTACATCGAACTGGATCTCAACAGCGGTAAGATCCTTGAGAG
241 ---------+---------+---------+---------+---------+---------+ 300
    CAACCCACGTGCTCACCCAATGTAGCTTGACCTAGAGTTGTCGCCATTCTAGGAACTCTC

MboII
              TaiI
              XmnI            DraI
              AciI            MseI                        AciI
           Bce83I           BsiHKAI                       HhaI
              ||            Bsp1286I                      ThaI
              ||                 |                         |
    TTTTCGCCCCGAAGAACGTTTTCCAATGATGAGCACTTTTAAAGTTCTGCTATGTGGCGC
```

Fig. 1(cont.)

```
301 ---------+---------+---------+---------+---------+---------+ 360
    AAAAGCGGGGCTTCTTGCAAAAGGTTACTACTCGTGAAAATTTCAAGACGATACACCGCG

HgaI
                            TaqII
                    NciI
                    ScrFI                    AciI
                    MspI                     Fnu4HI              BseMII
                    BcgI                     TauI                DdeI
        BscGI   BsaHI                        BsiEI           BcgI
        |       |   |||||                    ||||            |  ||
    GGTATTATCCCGTATTGACGCCGGGCAAGAGCAACTCGGTCGCCGCATACACTATTCTCA
361 ---------+---------+---------+---------+---------+---------+ 420
    CCATAATAGGGCATAACTGCGGCCCGTTCTCGTTGAGCCAGCGGCGTATGTGATAAGAGT

RsaI
                ScaI    MaeIII                              FokI
                TatI    Tsp45I                          BccI    Bst4CI
            HphI|       BsrI                       SfaNI|  NlaIII|
             |  ||      ||                          |   |  || ||
    GAATGACTTGGTTGAGTACTCACCAGTCACAGAAAAGCATCTTACGGATGGCATGACAGT
421 ---------+---------+---------+---------+---------+---------+ 480
    CTTACTGAACCAACTCATGAGTGGTCAGTGTCTTTTCGTAGAATGCCTACCGTACTGTCA

CviJI
                                                    HaeIII
                                                    TspRI
                                                    EaeI
                                                    Fnu4HI
                        TspRI                       GdiII
                        Fnu4HI                      TauI
                        TseI                        AciI
    Tsp509I     BtsI               NlaIII       BtsI
      BbvI|    CviRI                MslI        CjePI
    |   ||    |  ||                 |           | ||||||
    AAGAGAATTATGCAGTGCTGCCATAACCATGAGTGATAACACTGCGGCCAACTTACTTCT
481 ---------+---------+---------+---------+---------+---------+ 540
    TTCTCTTAATACGTCACGACGGTATTGGTACTCACTATTGTGACGCCGGTTGAATGAAGA

AvaII
                Sau96I
                CjePI                                       AlwI
        BsiEI                                               NlaIII
        PvuI                                                MaeIII
        DpnI                                                DpnI
    Sau3AI      AluI    TaqII                           Sau3AI
    MnlI|       CviJI   AciI|       CviRI   NlaIII         |||
    |   ||||    |       |   |       |       |              ||||
    GACAACGATCGGAGGACCGAAGGAGCTAACCGCTTTTTTGCACAACATGGGGGATCATGT
541 ---------+---------+---------+---------+---------+---------+ 600
    CTGTTGCTAGCCTCCTGGCTTCCTCGATTGGCGAAAAAACGTGTTGTACCCCCTAGTACA

AceIII    MspI                                SfaNI
            DpnI   BsaWI|  AluI                         MaeIII
        Sau3AI |   NlaIV| CviJI       CviJI             Tsp45I
            ||||    |||   ||           |                  |||
    AACTCGCCTTGATCGTTGGGAACCGGAGCTGAATGAAGCCATACCAAACGACGAGCGTGA
601 ---------+---------+---------+---------+---------+---------+ 660
    TTGAGCGGAACTAGCAACCCTTGGCCTCGACTTACTTCGGTATGGTTTGCTGCTCGCACT

HhaI
                                FspI
                            TaiI
        MslI    SfcI   BsrDI AclI |    MseI        BsrI
        |       |       |    |   ||    |           |
    CACCACGATGCCTGTAGCAATGGCAACAACGTTGCGCAAACTATTAACTGGCGAACTACT
661 ---------+---------+---------+---------+---------+---------+ 720
    GTGGTGCTACGGACATCGTTACCGTTGTTGCAACGCGTTTGATAATTGACCGCTTGATGA
                                                        MseI
```

Fig.1(cont.)

```
                        VspI
         AluI  MspI Tsp509I
         CviJI  NciI                    BccI                   AvaII
         BfaI  |ScrFI              MnlI  BsrI  EciI           Sau96I
           |    | |                  |    |  AciI|FokI         CviRI
           |    | |                  |    |    | |  |            |
      TACTCTAGCTTCCCGGCAACAATTAATAGACTGGATGGAGGCGGATAAAGTTGCAGGACC
721   ---------+---------+---------+---------+---------+---------+ 780
      ATGAGATCGAAGGGCCGTTGTTAATTATCTGACCTACCTCCGCCTATTTCAACGTCCTGG

CviJI
                          Cac8I
              CviJI       CviJI
              HaeIII      BglI                              MspI
              Sau96I      MspI                              BsrFI
              HhaI        MwoI                              CviJI
                |  |        |  |                            NlaIV
                |  |        |  |                              | |
      ACTTCTGCGCTCGGCCCTTCCGGCTGGCTGGTTTATTGCTGATAAATCTGGAGCCGGTGA
781   ---------+---------+---------+---------+---------+---------+ 840
      TGAAGACGCGAGCCGGGAAGGCCGACCGACCAAATAACGACTATTTAGACCTCGGCCACT

BccI
                 AciI                       BfiI
                 BsaI                       BbvI
                 BsmAI                      CviJI
                 ThaI                       HaeIII
           BpmI                             BsrI
           HphI                             NlaIV
           SimI          Fnu4HI             TspRI             Pfl1108I
       Hin4I |   |     BsrDI|TseI         Sau96I| CviJI BscGI MnlI|
         |   |   |       |  | |             |   |  |     |    |  |
      GCGTGGGTCTCGCGGTATCATTGCAGCACTGGGGCCAGATGGTAAGCCCTCCCGTATCGT
841   ---------+---------+---------+---------+---------+---------+ 900
      CGCACCCAGAGCGCCATAGTAACGTCGTGACCCCGGTCTACCATTCGGGAGGGCATAGCA

HinfI
           AhdI
           HaeIV
           Hin4I                                        BseMII
           BscGI                            DpnI
           |||||              PleI          Sau3AI
           |||||               |            FokI  |  DdeI
           |||||               |              |   |   |
      AGTTATCTACACGACGGGGAGTCAGGCAACTATGGATGAACGAAATAGACAGATCGCTGA
901   ---------+---------+---------+---------+---------+---------+ 960
      TCAATAGATGTGCTGCCCCTCAGTCCGTTGATACCTACTTGCTTTATCTGTCTAGCGACT MnlI            Bst4CI
           NlaIV     MseI            CjePI
           BanI   | TspRI  MaeIII      |
             | |    |        |         |
      GATAGGTGCCTCACTGATTAAGCATTGGTAACTGTCAGACCAAGTTTACTCATATATACT
961   ---------+---------+---------+---------+---------+---------+ 1020
      CTATCCACGGAGTGACTAATTCGTAACCATTGACAGTCTGGTTCAAATGAGTATATATGA DpnI
                                                 BstYI
                                                 Sau3AI
                                                 AlwI
                                                 AlwI
                                              BfaI
                                              DpnI
                                              BstYI
                                              Sau3AI
              DraI       Tsp509I DraI                           MboII
       CjePI  MseI        MseI  MseI                            HphI
         |     |            |    |                                |
      TTAGATTGATTTAAAAACTTCATTTTTAATTTAAAAGGATCTAGGTGAAGATCCTTTTTGA
1021  ---------+---------+---------+---------+---------+---------+ 1080
      AATCTAACTAAATTTTGAAGTAAAAATTAAATTTTCCTAGATCCACTTCTAGGAAAAACT
                                HgaI
```

Fig.1(cont.)

```
                                      UbaLI
                                      Bsp24I
                                      CjePI            TspRI
            NlaIII                    CjeI    BseMII             BscGI
            RcaI          MseI   TaiI         DdeI      SimI
             |             |      |    |       |         |         |
      TAATCTCATGACCAAAATCCCTTAACGTGAGTTTTCGTTCCACTGAGCGTCAGACCCCGT
1081  ------------+------------+------------+------------+------------+------------+  1140
      ATTAGAGTACTGGTTTTAGGGAATTGCACTCAAAAGCAAGGTGACTCGCAGTCTGGGGCA

DpnI
                  BstYI
                  Sau3AI
            MboII         DpnI                                       CviRI
            DpnI          BstYI         Tth111II                     Cac8I
      Sau3AI              Sau3AI        Bce83I                       Fnu4HI
      CjeI                AlwI          HhaI                          TseI
      CjePI               SmlI          ThaI
      Bsp24I              AlwI          BbvI     MwoI
        |                  |              |       |                    |
      AGAAAAGATCAAAGGATCTTCTTGAGATCCTTTTTTTCTGCGCGTAATCTGCTGCTTGCA
1141  ------------+------------+------------+------------+------------+------------+  1200
      TCTTTTCTAGTTTCCTAGAAGAACTCTAGGAAAAAAGACGCGCATTAGACGACGAACGT

EgiEII                        AluI
                            AciI                          CviJI
                            MspA1I                        AlwI
                     Tth111II                             CjeI
                     AciI                                 CjeI
             CjeI                                         DpnI
             CjeI                                  Sau3AI
             CjeI                                  MspI                CjePI
              |                 |                   |                    |
      AACAAAAAAACCACCGCTACCAGCGGTGGTTTGTTTGCCGGATCAAGAGCTACCAACTCT
1201  ------------+------------+------------+------------+------------+------------+  1260
      TTGTTTTTTTGGTGGCGATGGTCGCCACCAAACAAACGGCCTAGTTCTCGATGGTTGAGA

CjePI
                                     HhaI
                                     Bsp24I
            MaeIII          BsrI     CjePI           Bcef I
      Eco57I         CviJI           CjeI     Bst4CI        Bfa I
        |             |                |         |           |
      TTTTCCGAAGGTAACTGGCTTCAGCAGAGCGCAGATACCAAATACTGTCCTTCTAGTGTA
1261  ------------+------------+------------+------------+------------+------------+  1320
      AAAAGGCTTCCATTGACCGAAGTCGTCTCGCGTCTATGGTTTATGACAGGAAGATCACAT CjeI     CviJI
      CjePI    HaeI
      Bsp24I   HaeIII
      CviJI    BslI            SfcI       AciI                MnlI
        |       |                |         |                    |
      GCCGTAGTTAGGCCACCACTTCAAGAACTCTGTAGCACCGCCTACATACCTCGCTCTGCT
1321  ------------+------------+------------+------------+------------+------------+  1380
      CGGCATCAATCCGGTGGTGAAGTTCTTGAGACATCGTGGCGGATGTATGGAGCGAGACGA BsrI
                      Fnu4HI
                      TseI
                      Fnu4HI
                      TspRI
                      AlwNI                               PleI
              BbvI    CviJI                               NciI
        MaeIII        TseI                                ScrFI       SmlI
        BbvI    BsrI                    MmeI              MspI        HinfI
        BbvI    |                       TspRI      Bce83I  |
          |     |                         |           |    |
      AATCCTGTTACCAGTGGCTGCTGCCAGTGGCGATAAGTCGTGTCTTACCGGGTTGGACTC
1381  ------------+------------+------------+------------+------------+------------+  1440
      TTAGGACAATGGTCACCGACGACGGTCACCGCTATTCAGCACAGAATGGCCCAACCTGAG
                                                 BbvI
```

Fig.1(cont.)

```
                                      CviJI
                               BsiEI |
                            AciI  |  |                     BsiHKAI
                          MspAlI  |  |                     Bsp1286I
                  MspI    Fnu4HI  |  |                      BseSI
                  BsaWI   HhaI |  |  |                      CviRI
         MaeIII   |  |    TseI |  |  |          BscGI       ApaLI  |
         |        |  |    |    |  |  |          |           |      |
         AAGACGATAGTTACCGGATAAGGCGCAGCGGTCGGGCTGAACGGGGGGTTCGTGCACACA
   1441  ---------+---------+---------+---------+---------+---------+  1500
         TTCTGCTATCAATGGCCTATTCCGCGTCGCCAGCCCGACTTGCCCCCCAAGCACGTGTGT

AluI
              CviJI                   BseMII
      CviJI   |                       DdeI|     SfcI
      |       |                       |   |     |
      GCCCAGCTTGGAGCGAACGACCTACACCGAACTGAGATACCTACAGCGTGAGCATTGAGA
   1501 ---------+---------+---------+---------+---------+---------+  1560
      CGGGTCGAACCTCGCTTGCTGGATGTGGCTTGACTCTATGGATGTCGCACTCGTAACTCT

Fnu4HI
                                                     TauI
                                             MspI    AciI
                                             BsaWI|  BciVI
      HaeII                    EcoI          MmeI| | BslI
      HhaI                     AciI          |   | | |        SimI
      |                        |             |   | | |        |
      AAGCGCCACGCTTCCCGAAGGGAGAAAGGCGGACAGGTATCCGGTAAGCGGCAGGGTCGG
   1561 ---------+---------+---------+---------+---------+---------+  1620
      TTCGCGGTGCGAAGGGCTTCCCTCTTTCCGCCTGTCCATAGGCCATTCGCCGTCCCAGCC

ScrFI
                   BsaJI|
             BsssI EcoRII|
             HhaI  AluI |           ScrFI
         MnlI|   | CviJI|           EcoRII
         |   |   | |    |           |
         AACAGGAGAGCGCACGAGGGAGCTTCCAGGGGGAAACGCCTGGTATCTTTATAGTCCTGT
   1621 ---------+---------+---------+---------+---------+---------+  1680
         TTGTCCTCTCGCGTGCTCCCTCGAAGGTCCCCCTTTGCGGACCATAGAAATATCAGGACA CviJI
                   DrdI                                         NlaIV|
                   MnlI|SfaNI                                   EciI |
         HgaI  SmlI |  |TaqI          Bce83I              AciI       |
         |     |   |  ||              |                  |           |
         CGGGTTTCGCCACCTCTGACTTGAGCGTCGATTTTTGTGATGCTCGTCAGGGGGGCGGAG
   1681 ---------+---------+---------+---------+---------+---------+  1740
         GCCCAAAGCGGTGGAGACTGAACTCGCAGCTAAAAACACTACGAGCAGTCCCCCCGCCTC CviJI
                    HaeIII             CviJI
                    CjeI               HaeI
                    Fnu4HI             HaeIII
                    TauI     ScrFI              CjeI
                    AciI     EcoRII             CviJI
                    ThaI     NlaIV              HaeI
                    MwoI  | Bst4CI              HaeIII
            Cac8I   |  |  | BslI           Cac8I|
            |       |  |  | |              |    |  BslI
            CCTATGGAAAAACGCCAGCAACGCGGCCTTTTTACGGTTCCTGGCCTTTTGCTGGCCTTT
   1741 ---------+---------+---------+---------+---------+---------+  1800
            GGATACCTTTTTGCGGTCGTTGCGCCGGAAAAATGCCAAGGACCGGAAAACGACCGGAAA NlaIII
               NspI
         AflIII |                HinfI                    AceIII
         BspLU11I|                TfiI       Bst4CI       AciI
         |       |                |          |            |
         TGCTCACATGTTCTTTCCTGCGTTATCCCCTGATTCTGTGGATAACCGTATTACCGCCTT
   1801 ---------+---------+---------+---------+---------+---------+  1860
```

Fig.1(cont.)

```
                  AlwI
              HindIII
                 MwoI
                 DpnI
         Sau3AI
           AciI
         MspAlI
         Fnu4HI
          CviRI
           TseI
         ATGcagcGGATCAAGCTTGGATCCATCGATGAATTCGGCGCGCCACTAGTGCCGGCCTGC
1981     ---------+---------+---------+---------+---------+---------+ 2040
         TACgtcgCCTAGTTCGAACCTAGGTAGCTACTTAAGCCGCGCGGTGATCACGGCCGGACG PleI
                       AciI
                      BsiEI
               HincII
                AccI
                TaqI
                 SalI
           HinfI
         BfaI
          XbaI
         PstI         SimI     Hin4I
         AGTCTAGAGTCGACCGCAAGACCCTTCCTCTATATAAGGAAGTTCATTTCATTTGGAGAG
2041     ---------+---------+---------+---------+---------+---------+ 2100
         TCAGATCTCAGCTGGCGTTCTGGGAAGGAGATATATTCCTTCAAGTAAAGTAAACCTCTC AvaII
                       NlaIII
                       Sau96I
                  BsaJI
                  BstDSI
                CviJI
                 HaeI
                 HaeIII
                  MscI
                EaeI
                 MwoI
         Bsp24I
          CjePI
           CjeI
          TaqI                                BscGI
          AvaI                                CjeI                Bsp24I
          SmlI           NcoI                 CjePI               CjeI
          XhoI           StyI       SfcI      Bsp24I              CjePI
         GACACGCTCGAGTGGCCACCATGGTCCGTCCTGTAGAAACCCCAACCCGTGAAATCAAAA
2101     ---------+---------+---------+---------+---------+---------+ 2160
         CTGTGCGAGCTCACCGGTGGTACCAGGCAGGACATCTTTGGGGTTGGGCACTTTAGTTTT DpnI
                                                             BclI
                                                             Sau3AI
                                                           Tsp509I
                                                         Bst4CI
                                                      AlwI
                                                   NruI
                                                   ThaI
                                              CjeI
                                              DpnI
                                             CjePI
                                          Bsp24I
         TaqI CviJI        BcefI
         RleAI HaeIII  BsmI     Sau3AI        CjePI
         AACTCGACGGCCTGTGGGCATTCAGTCTGGATCGCGAAAACTGTGGAATTGATCAGCGTT
```

Fig.1(cont.)

```
2161 ----------+---------+---------+---------+---------+---------+ 2220
     TTGAGCTGCCGGACACCCGTAAGTCAGACCTAGCGCTTTTGACACCTTAACTAGTCGCAA

MunI
                            Tsp509I
               CjePI        NciI                                     SfaNI
               MaeIII       ScrFI                                    DpnI
               HhaI         MspI              ScrFI                  Sau3AI
               ThaI         CviJI    EcoRII                  MseI
     GGTGGGAAAGCGCGTTACAAGAAAGCCGGGCAATTGCTGTGCCAGGCAGTTTTAACGATC
2221 ----------+---------+---------+---------+---------+---------+ 2280
     CCACCCTTTCGCGCAATGTTCTTTCGGCCCGTTAACGACACGGTCCGTCAAAATTGCTAG

FauI      Cac8I                      HhaI
     CviRI    Tsp509I   AciI     TaiI              ThaI
     AGTTCGCCGATGCAGATATTCGTAATTATGCGGGCAACGTCTGGTATCAGCGCGAAGTCT
2281 ----------+---------+---------+---------+---------+---------+ 2340
     TCAAGCGGCTACGTCTATAAGCATTAATACGCCCGTTGCAGACCATAGTCGCGCTTCAGA

Cac8I
                BbvI
                CviJI
                HaeI        Fnu4HI
                HaeIII      SfaNI         MaeIII
                Cac8I       TseI          Tsp45I
                      MwoI       TaqI     AciI       RleAI
     TTATACCGAAAGGTTGGGCAGGCCAGCGTATCGTGCTGCGTTTCGATGCGGTCACTCATT
2341 ----------+---------+---------+---------+---------+---------+ 2400
     AATATGGCTTTCCAACCCGTCCGGTCGCATAGCACGACGCAAAGCTACGCCAGTGAGTAA

CviJI
                                                 Fnu4HI
                              HaeIV              SfaNI
                BcefI         Hin4I              TauI
                SimI          BccI               AciI
     ACGGCAAAGTGTGGGTCAATAATCAGGAAGTGATGGAGCATCAGGGCGGCTATACGCCAT
2401 ----------+---------+---------+---------+---------+---------+ 2460
     TGCCGTTTCACACCCAGTTATTAGTCCTTCACTACCTCGTAGTCCCGCCGATATGCGGTA TaiI
         MaeIII                                BsaAI
         Tsp45I                NciI            SnaBI
       CviJI                   ScrFI           RsaI
     BcefI                     MspI    HphI        Bst4CI  CjePI
     TTGAAGCCGATGTCACGCCGTATGTTATTGCCGGGAAAAGTGTACGTATCACCGTTTGTG
2461 ----------+---------+---------+---------+---------+---------+ 2520
     AACTTCGGCTACAGTGCGGCATACAATAACGGCCCTTTTCACATGCATAGTGGCAAACAC FauI
                         NciI
                         ScrFI
                         CjePI
                         MspI
            BsrI    AciI                              HphI
     TGAACAACGAACTGAACTGGCAGACTATCCCGCCGGGAATGGTGATTACCGACGAAAACG
2521 ----------+---------+---------+---------+---------+---------+ 2580
     ACTTGTTGCTTGACTTGACCGTCTGATAGGGCGGCCCTTACCACTAATGGCTGCTTTTGC HinfI     Fnu4HI
                                           TfiI      TseI
        BcefI       NlaIII   MseI      MspI    BccI
     GCAAGAAAAAGCAGTCTTACTTCCATGATTTCTTTAACTATGCCGGAATCCATCGCAGCG
2581 ----------+---------+---------+---------+---------+---------+ 2640
     CGTTCTTTTTCGTCAGAATGAAGGTACTAAAGAAATTGATACGGCCTTAGGTAGCGTCGC
```

Fig.1(cont.)

```
                                                                    MaeIII         ThaI
                                                                    Tsp45I         HgaI
                                                                    MslI           HphI
                                              MslI           Bst4CI                MwoI
                                              ScrFI          BsaJI                 NlaIII
                                              BsaJI          BstDSI                NspI
        BbvI      TaqII  EcoRII     HphI EcoRV                          PshAI
           |         |      |          |   |                               |
        TAATGCTCTACACCACGCCGAACACCTGGGTGGACGATATCACCGTGGTGACGCATGTCG
2641    ------------+---------+---------+---------+---------+---------+ 2700
        ATTACGAGATGTGGTGCGGCTTGTGGACCCACCTGCTATAGTGGCACCACTGCGTACAGC

CviJI
                                                     HaeI
             Bst4CI                              HaeIII
             MaeIII  AflIII       ThaI    AarI  MscI
        Hhal HgaI    MluI  HincII BspMI BsrI EaeI                    HphI
           |    |       |      |     |    |  |                         |
        CGCAAGACTGTAACCACGCGTCTGTTGACTGGCAGGTGGTGGCCAATGGTGATGTCAGCG
2701    ----------+---------+---------+---------+---------+---------+ 2760
        GCGTTCTGACATTGGTGCGCAGACAACTGACCGTCCACCACCGGTTACCACTACAGTCGC DpnI
                      Sau3AI
                      BsaBI                       BsrI     AciI
        SfaNI         AciI     AlwI  CviRI BspGI  |FauI   BfaI
           |            |        |      |     |   |  |      |
        TTGAACTGCGTGATGCGGATCAACAGGTGGTTGCAACTGGACAAGGCACTAGCGGGACTT
2761    ----------+---------+---------+---------+---------+---------+ 2820
        AACTTGACGCACTACGCCTAGTTGTCCACCAACGTTGACCTGTTCCGTGATCGCCCTGAA NciI
             HinfI                 ScrFI                             MaeIII
              TfiI       MwoI      MnlI              HgaI            Tsp45I
        CviRI BsmFI AciI HphI      MspI  BslI        HphI   Bst4CI
           |    |     |    |         |     |           |      |
        TGCAAGTGGTGAATCCGCACCTCTGGCAACCGGGTGAAGGTTATCTCTATGAACTGTGCG
2821    ----------+---------+---------+---------+---------+---------+ 2880
        ACGTTCACCACTTAGGCGTGGAGACCGTTGGCCCACTTCCAATAGAGATACTTGACACGC CjeI
                              AciI
        CviJI               HgaI       FauI    MspI  BslI
        CjeI    CviJI       EcoRV |FokI ThaI   BsaWI|SfaNI
          |       |           |   |  |    |      |   |
        TCACAGCCAAAAGCCAGACAGAGTGTGATATCTACCCGCTTCGCGTCGGCATCCGGTCAG
2881    ----------+---------+---------+---------+---------+---------+ 2940
        AGTGTCGGTTTTCGGTCTGTCTCACACTATAGATGGGCGAAGCGCAGCCGTAGGCCAGTC AlwNI                                    CjeI
             BtsI           CjeI                   CjeI              BsrI
        TspRI|TspRI   Bst4CI| MseI        Bst4CI       CviJI
           |   |         |    |              |           |  |
        TGGCAGTGAAGGGCGAACAGTTCCTGATTAACCACAAACCGTTCTACTTTACTGGCTTTG
2941    ----------+---------+---------+---------+---------+---------+ 3000
        ACCGTCACTTCCCGCTTGTCAAGGACTAATTGGTGTTTGGCAAGATGAAATGACCGAAAC BsiHKAI
                                                             Bsp1286I
                                                             BseSI
                                                             CviRI
             MslI      MboII                                 ApaLI
             NlaIII    BcgI             TaqI                 MwoI
        RcaI       AciI                HinfI                 BccI
        SfaNI      CjeI                 TfiI      TaiI  BcgI
           |         |  |                 |           |    |
        GTCGTCATGAAGATGCGGACTTGCGTGGCAAAGGATTCGATAACGTGCTGATGGTGCACG
3001    ----------+---------+---------+---------+---------+---------+ 3060
        CAGCAGTACTTCTACGCCTGAACGCACCGTTTCCTAAGCTATTGCACGACTACCACGTGC
```

Fig.1(cont.)

```
                              CviJI
                              HaeIII
                              NlaIV                                EarI
            MseI              Sau96I             RsaI              SfaNI
            VspI        BsrI              Bst4CI          MnlI
            ACCACGCATTAATGGACTGGATTGGGGCCAACTCCTACCGTACCTCGCATTACCCTTACG
     3061   ---------+---------+---------+---------+---------+---------+  3120
            TGGTGCGTAATTACCTGACCTAACCCCGGTTGAGGATGGCATGGAGCGTAATGGGAATGC

BfiI                    BbvI                Fnu4HI
              MboII Eco57I                         SfaNI               TseI
              TaqI  | BsrI           NlaIII   MslI        HphI
            CTGAAGAGATGCTCGACTGGGCAGATGAACATGGCATCGTGGTGATTGATGAAACTGCTG
     3121   ---------+---------+---------+---------+---------+---------+  3180
            GACTTCTCTACGAGCTGACCCGTCTACTTGTACCGTAGCACCACTAACTACTTTGACGAC

NspV
                  MseI               TaqI   Cac8I          CviJI
            CviJI |BcgI     MnlI     FauI | AciI  |        BcgI
            CTGTCGGCTTTAACCTCTCTTTAGGCATTGGTTTCGAAGCGGGCAACAAGCCGAAAGAAC
     3181   ---------+---------+---------+---------+---------+---------+  3240
            GACAGCCGAAATTGGAGAGAAATCCGTAACCAAAGCTTCGCCCGTTGTTCGGCTTTCTTG

MnlI
            EarI
            RsaI
            BsrGI               BscGI
            Bst4CI        MboII       BseMII     HhaI
            TatI          HincII      DdeI|Cac8I      AceIII      MseI
            TGTACAGCGAAGAGGCAGTCAACGGGGAAACTCAGCAAGCGCACTTACAGGCGATTAAAG
     3241   ---------+---------+---------+---------+---------+---------+  3300
            ACATGTCGCTTCTCCGTCAGTTGCCCCTTTGAGTCGTTCGCGTGAATGTCCGCTAATTTC MaeIII
                    Tsp45I                                         MspI
                    HhaI                                           BsaWI
            AluI    ThaI                               BciVI
            CviJI   MwoI       CjeI      BslI   TaqII  HphI CjeI
            AGCTGATAGCGCGTGACAAAAACCACCCAAGCGTGGTGATGTGGAGTATTGCCAACGAAC
     3301   ---------+---------+---------+---------+---------+---------+  3360
            TCGACTATCGCGCACTGTTTTTGGTGGGTTCGCACCACTACACCTCATAACGGTTGCTTG BscGI
                           BsiHKAI              BsrI
                           Bsp1286I             EciI
                           BseSI                TspRI
                     AciI  CviRI         HhaI   AciI     ThaI
              BscGI        ApaLI   SspI  ThaI|MwoI       AflIII
                                                         MluI
            CGGATACCCGTCCGCAAGGTGCACGGGAATATTTCGCGCCACTGGCGGAAGCAACGCGTA
     3361   ---------+---------+---------+---------+---------+---------+  3420
            GCCTATGGGCAGGCGTTCCACGTGCCCTTATAAAGCGCGGTGACCGCCTTCGTTGCGCAT DpnI
                            HgaI
                            Sau3AI
                            HgaI
                      HphI  ThaI
            SimI      AflIII                                        HgaI
            TaqI|     MluI                                           CjePI
            HgaI|                    AarI     BspMI
            AACTCGACCCGACGCGTCCGATCACCTGCGTCAATGTAATGTTCTGCGACGCTCACACCG
     3421   ---------+---------+---------+---------+---------+---------+  3480
```

Fig.1(cont.)

```
                TTGAGCTGGGCTGCGCAGGCTAGTGGACGCAGTTACATTACAAGACGCTGCGAGTGTGGC
                              DpnI                                  HaeIV
                     Sau3AI                                          Hin4I
               BccI    |       CjePI    Bst4CI                 BccI  |
               ATACCATCAGCGATCTCTTTGATGTGCTGTGCCTGAACCGTTATTACGGATGGTATGTCC
         3481  --------+---------+---------+---------+---------+---------+ 3540
               TATGGTAGTCGCTAGAGAAACTACACGACACGGACTTGGCAATAATGCCTACCATACAGG

ScrFI
                Fnu4HI                                          CviJI
                 TauI                          BsrI             EcoRII
                 AciI                   BcefI                   HaeI
                FokI                    RsaI                    HaeIII
               AAAGCGGCGATTTGGAAACGGCAGAGAAGGTACTGGAAAAGAACTTCTGGCCTGGCAGG
         3541  --------+---------+---------+---------+---------+---------+ 3600
               TTTCGCCGCTAAACCTTTGCCGTCTCTTCCATGACCTTTTTCTTGAAGACCGGACCGTCC CviRI
                                                                     Fnu4HI
                                                                     CviJI
                                                                     TseI
                                                                     NciI
                                                                     ScrFI
                                BsaBI                                MspI
                                 HphI                                CviJI
                                 SfaNI                 BbvI    BcefI
                  CviRI CviJI          BciVI           BsgI    TaiI
               AGAAACTGCATCAGCCGATTATCATCACCGAATACGGCGTGGATACGTTAGCCGGGCTGC
         3601  --------+---------+---------+---------+---------+---------+ 3660
               TCTTTGACGTAGTCGGCTAATAGTAGTGGCTTATGCCGCACCTATGCAATCGGCCCGACG EarI
                                 NlaIII
                                 NspI
                                 BslI
                          AflIII                        CviJI
                          BspLU11I                      NlaIII
                    RsaI                       CviRI           BsaBI
                   BsrGI                       TspRI           HgaI
                   TatI    MslI         MboII                  HphI
               ACTCAATGTACACCGACATGTGGAGTGAAGAGTATCAGTGTGCATGGCTGGATATGTATC
         3661  --------+---------+---------+---------+---------+---------+ 3720
               TGAGTTACATGTGGCTGTACACCTCACTTCTCATAGTCACACGTACCGACCTATACATAG ThaI
                HgaI    DpnI         CjePI                ApoI
                ThaI    Sau3AI       HaeII              Tsp509I      CjePI
               AciI     BcefI        HhaI                HphI        MwoI
               ACCGCGTCTTTGATCGCGTCAGCGCCGTCGTCGGTGAACAGGTATGGAATTTCGCCGATT
         3721  --------+---------+---------+---------+---------+---------+ 3780
               TGGCGCAGAAACTAGCGCAGTCGCGGCAGCAGCCACTTGTCCATACCTTAAAGCGGCTAA AlwI
                                                             Hin4I
                                                             DpnI
                                            BstYI
                               HhaI         Sau3AI
                               ThaI  MaeIII MboII            NruI
                       MnlI MwoI |   AciI   |                ThaI
               TTGCGACCTCGCAAGGCATATTGCGCGTTGGCGGTAACAAGAAAGGGATCTTCACTCGCG
         3781  --------+---------+---------+---------+---------+---------+ 3840
               AACGCTGGAGCGTTCCGTATAACGCGCAACCGCCATTGTTCTTTCCCTAGAAGTGAGCGC
                         CviJI
```

Fig. 1(cont.)

```
                    Fnu4HI
                    TauI           CviRI           MwoI
       AciI         AciI           Fnu4HI    BspGI      NlaIII
       BsiEI        BbvI           TseI  BcgI          BsrI
       ACCGCAAACCGAAGTCGGCGGCTTTTCTGCTGCAAAAACGCTGGACTGGCATGAACTTCG
  3841 --------+---------+---------+---------+---------+---------+ 3900
       TGGCGTTTGGCTTCAGCCGCCGAAAAGACGACGTTTTTGCGACCTGACCGTACTTGAAGC

BslI
         BcgI
         Fnu4HI                                ScrFI
         HphI                                  EcoRII
         MnlI                              BcgI
         TseI                         Tth111II
       AciI       BbvI       HinfI                          BccI
                             TfiI                      HhaI
       GTGAAAAACCGCAGCAGGGAGGCAAACAATGAATCAACAACTCTCCTGGCGCACCATCGT
  3901 --------+---------+---------+---------+---------+---------+ 3960
       CACTTTTTGGCGTCGTCCCTCCGTTTGTTACTTAGTTGTTGAGAGGACCGCGTGGTAGCA Tsp509I
                                              NlaIII
                                             RcaI
                                             DpnI
                                            BclI
                                            Sau3AI
                                            KpnI
                                           NlaIV
                                           RsaI
                                          BanI
                                          NciI
                                          ScrFI
                                          SmaI
                                          MspI
                                          NciI
                                          ScrFI
                                          AvaI
                                          BsaJI
                                          BanII
                 Tsp509I                   BsiHKAI
                 AvaI                      Bsp1286I
                 BsaJI                     SacI
                 CviJI                     AluI                TaqI
         SfcI          BcgI MnlI           CviJI               AluI CviJI
       CGCTACAGCCTCGGGAATTGCTACCGAGCTcccgggtacctgatcatgagtaattagctC
  3961 --------+---------+---------+---------+---------+---------+ 4020
       GCGATGTCGGAGCCCTTAACGATGGCTCGAgggcccatggactagtactcattaatcgaG BsiEI
               PvuI                    MseI                MspI
       ApoI    DpnI              AflII         HinfI      BslI
       Tsp509I Sau3AI     Tth111II SmlI        TfiI       BsrFI
       GAATTTCCCCGATCGTTCAAACATTTGGCAATAAAGTTTCTTAAGATTGAATCCTGTTGC
  4021 --------+---------+---------+---------+---------+---------+ 4080
       CTTAAAGGGGCTAGCAAGTTTGTAAACCGTTATTTCAAAGAATTCTAACTTAGGACAACG AflIII
                                                          BspLU11I
                                                          MseI
                                                   Tsp509I
                                              MseI NlaIII
       MwoI   BsaBI  Tsp509I  Tsp509I         TaiI NspI
       CGGTCTTGCGATGATTATCATATAATTTCTGTTGAATTACGTTAAGCATGTAATAATTAA
  4081 --------+---------+---------+---------+---------+---------+ 4140
       GCCAGAACGCTACTAATAGTATATTAAAGACAACTTAATGCAATTCGTACATTATTAATT
```

Fig.1(cont.)

```
                 NlaIII
                 NsiI
              CviRI
     NlaIII   |  |            BsmFI             PleI
     NspI  |  |  | TaiI     BccI          HinfI Tsp509I      FauI
        |  |  |  |  |          |            |   AciI          |
        CATGTAATGCATGACGTTATTTATGAGATGGGTTTTTATGATTAGAGTCCCGCAATTATA
4141    ---------+---------+---------+---------+---------+---------+ 4200
        GTACATTACGTACTGCAATAAATACTCTACCCAAAAATACTAATCTCAGGGCGTTAATAT
```

```
                                                          AciI
                                                          HhaI
                                                          ThaI
                                           HhaI           Cac8I |
                                           Cac8I    HaeIV  HhaI |
                                           HhaI     Hin4I  ThaI |
                                           ThaI     Tsp509I BssHII|
         MseI   ThaI              BssHII | BfaI          |  ThaI|
           |     |                  |    |  |            |    | |
        CATTTAATACGCGATAGAAAACAAAATATAGCGCGCAAACTAGGATAAATTATCGCGCGC
4201    ---------+---------+---------+---------+---------+---------+ 4260
        GTAAATTATGCGCTATCTTTTGTTTTATATCGCGCGTTTGATCCTATTTAATAGCGCGCG
```

```
                             DpnI
                         BglII |
                         BstYI |
                         Sau3AI|
                   Tsp509I  |  |
                   DpnI  |  |  |        Cac8I
                   Sau3AI|  |  |        BfaI
            MaeIII BfaI| |  |  |        NheI|
              |     | ||  |  |  |         | |
        GGTGTCATCTATGTTACTAGATCGGGaattagatctgctagc
4261    ---------+---------+---------+---------+-- 4302
        CCACAGTAGATACAATGATCTAGCCCttaatctagacgatcg
```

Enzymes that do cut:

| | | | | | | | |
|---|---|---|---|---|---|---|---|
| AarI | AccI | AceIII | AciI | AclI | AflII | AflIII | AhdI |
| AluI | AlwI | AlwNI | ApaLI | ApoI | AscI | AvaI | AvaII |
| BamHI | BanI | BanII | BbvI | BccI | Bce83I | BcefI | BcgI |
| BciVI | BclI | BfaI | BfiI | BglI | BglII | BpmI | BsaI |
| BsaAI | BsaBI | BsaHI | BsaJI | BsaWI | BsaXI | BscGI | BseMII |
| BseSI | BsgI | BsiEI | BsiHKAI | BslI | BsmI | BsmAI | BsmFI |
| Bsp24I | Bsp1286I | BspGI | BspLU11I | BspMI | BsrI | BsrBI | BsrDI |
| BsrFI | BsrGI | BssHII | BssSI | Bst4CI | BstDSI | BstYI | BtsI |
| Cac8I | CjeI | CjePI | ClaI | CviJI | CviRI | DdeI | DpnI |
| DraI | DrdI | EaeI | EarI | EciI | Eco57I | EcoRI | EcoRII |
| EcoRV | FauI | Fnu4HI | FokI | FspI | GdiII | HaeI | HaeII |
| HaeIII | HaeIV | HgaI | HgiEII | HhaI | Hin4I | HincII | HindIII |
| HinfI | HphI | KpnI | MaeIII | MboII | MluI | MmeI | MnlI |
| MscI | MseI | MslI | MspI | MspAlI | MunI | MwoI | NciI |
| NcoI | NgoAIV | NheI | NlaIII | NlaIV | NruI | NsiI | NspI |
| NspV | Pfl108I | PleI | PshAI | PstI | PvuI | RcaI | RleAI |
| RsaI | SacI | SalI | SapI | Sau96I | Sau3AI | ScaI | ScrFI |
| SfaNI | SfcI | SimI | SmaI | SmlI | SnaBI | SpeI | SspI |
| StyI | TaiI | TaqI | TaqII | TatI | TauI | TfiI | ThaI |
| TseI | Tsp45I | Tsp509I | TspRI | Tth111II | UbaLI | VspI | XbaI |
| XhoI | XmnI | | | | | | |

Enzymes that do not cut:

| | | | | | | | |
|---|---|---|---|---|---|---|---|
| AatII | AloI | ApaI | AvrII | BaeI | BbsI | BbvCI | BmgI |
| BplI | Bpu10I | Bpu1102I | BsbI | BseRI | BsmBI | BspEI | BstAPI |
| BstEII | BstXI | BstZ17I | Bsu36I | DraIII | DrdII | EagI | Eco47III |
| EcoNI | EcoO109I | FseI | HpaI | NarI | NdeI | NotI | PacI |
| PflMI | PinAI | PmeI | PmlI | Psp5II | PvuII | RsrII | SacII |
| SanDI | SbfI | SexAI | SfiI | SgfI | SgrAI | SphI | SrfI |
| Sse8647I | StuI | SunI | SwaI | Tth111I | XcmI | | |

Summary of Expression Characteristics

| | Aerial parts | Roots | Wounding | Senescence | Peronospora Incompatible | Peronospora Compatible |
|---|---|---|---|---|---|---|
| 4 x S | Medium | Medium | + | nt | + | + |
| 4 x W2 | Medium | Very high | + | nt | + | + |
| 4 x GCC | Very high | Very high | + | nt | nt | nt |
| 4 x D | – | – | – | + | + | + |
| 4 x N | Medium | Medium | + | nt | + | + |
| 4 x W_Amy | Low | Low | nt | nt | + | + |
| 4 x W1 | Medium | Medium | + | nt | + | + |

Fig. 8

SEQUENCE LISTING

```
<160> NUMBER OF SEQ ID NOS: 35

<210> SEQ ID NO 1
<211> LENGTH: 7
<212> TYPE: DNA
<213> ORGANISM: Petroselinum crispum

<400> SEQUENCE: 1 tttgacc                                                              7

<210> SEQ ID NO 2
<211> LENGTH: 30
<212> TYPE: DNA
<213> ORGANISM: Petroselinum crispum

<400> SEQUENCE: 2
cacacttaat ttgaccgagt aacattcgcc                                    30

<210> SEQ ID NO 3
<211> LENGTH: 20
<212> TYPE: DNA
<213> ORGANISM: Petroselinum crispum
<220> FEATURE:
<221> NAME/KEY: misc_difference
<222> LOCATION: (8)..(14)
<223> OTHER INFORMATION: n=a,c,g,t, unknown or other

<400> SEQUENCE: 3
ttcagccnnn nnnnttgacc                                               20

<210> SEQ ID NO 4
<211> LENGTH: 29
<212> TYPE: DNA
<213> ORGANISM: Petroselinum crispum

<400> SEQUENCE: 4
ttattcagcc atcaaagttg accaataat                                     29

<210> SEQ ID NO 5
<211> LENGTH: 14
<212> TYPE: DNA
<213> ORGANISM: Triticum aestivum
<220> FEATURE:
<221> NAME/KEY: misc_difference
<222> LOCATION: (5)..(10)
<223> OTHER INFORMATION: n=a,c,g,t, unknown or other

<400> SEQUENCE: 5
tgacnnnnnn gtca                                                     14

<210> SEQ ID NO 6
<211> LENGTH: 14
<212> TYPE: DNA
<213> ORGANISM: Triticum aestivum
```

-continued

```
<400> SEQUENCE: 6
tgacttgacc gtca                                                  14

<210> SEQ ID NO 7
<211> LENGTH: 24
<212> TYPE: DNA
<213> ORGANISM: Petroselinum crispum

<400> SEQUENCE: 7
cagccaccaa agaggaccca gaat                                       24

<210> SEQ ID NO 8
<211> LENGTH: 16
<212> TYPE: DNA
<213> ORGANISM: Solanum tuberosum
<220> FEATURE:
<221> NAME/KEY: misc_difference
<222> LOCATION: (7)..(9)
<223> OTHER INFORMATION: n=a,c,g,t, unknown or other

<400> SEQUENCE: 8
gccaccnnnt ttgacc                                                16

<210> SEQ ID NO 9
<211> LENGTH: 25
<212> TYPE: DNA
<213> ORGANISM: Solanum tuberosum

<400> SEQUENCE: 9
ttctagccac cagatttgac caaac                                      25

<210> SEQ ID NO 10
<211> LENGTH: 24
<212> TYPE: DNA
<213> ORGANISM: Triticum aestivum

<400> SEQUENCE: 10
ggattgactt gaccgtcatc ggct                                       24

<210> SEQ ID NO 11
<211> LENGTH: 31
<212> TYPE: DNA
<213> ORGANISM: Petroselinum crispum

<400> SEQUENCE: 11
tacaattcaa acattgttca aacaaggaac c                               31

<210> SEQ ID NO 12
<211> LENGTH: 15
<212> TYPE: DNA
<213> ORGANISM: Petroselinum crispum

<400> SEQUENCE: 12
agttgaaatt caata                                                 15

<210> SEQ ID NO 13
<211> LENGTH: 30
<212> TYPE: DNA
<213> ORGANISM: Petroselinum crispum

<400> SEQUENCE: 13
agttgaaatt caataagttg aaattcaata                                 30
```

```
<210> SEQ ID NO 14
<211> LENGTH: 10
<212> TYPE: DNA
<213> ORGANISM: Petroselinum crispum
<220> FEATURE:
<221> NAME/KEY: misc_difference
<222> LOCATION: (9)..(9)
<223> OTHER INFORMATION: n=a,c,g,t, unknown or other

<400> SEQUENCE: 14 agccaccana                                                            10

<210> SEQ ID NO 15
<211> LENGTH: 27
<212> TYPE: DNA
<213> ORGANISM: Petroselinum crispum

<400> SEQUENCE: 15
tcaatatgtc aatggtcaac attcaac                                         27

<210> SEQ ID NO 16
<211> LENGTH: 21
<212> TYPE: DNA
<213> ORGANISM: Petroselinum crispum

<400> SEQUENCE: 16
tgtcaatggt caacattcaa c                                               21

<210> SEQ ID NO 17
<211> LENGTH: 4299
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 17
aggtggcact tttcggggaa atgtgcgcgg aaccccctatt tgtttatttt tctaaataca      60
ttcaaatatg tatccgctca tgagacaata accctgataa atgcttcaat aatattgaaa     120
aaggaagagt atgagtattc aacatttccg tgtcgccctt attccctttt ttgcggcatt     180
ttgccttcct gttttgctc acccagaaac gctggtgaaa gtaaaagatg ctgaagatca      240
gttgggtgca cgagtgggtt acatcgaact ggatctcaac agcggtaaga tccttgagag     300
ttttcgcccc gaagaacgtt ttccaatgat gagcactttt aaagttctgc tatgtggcgc     360
ggtattatcc cgtattgacg ccgggcaaga gcaactcggt cgccgcatac actattctca     420
gaatgacttg gttgagtact caccagtcac agaaaagcat cttacggatg gcatgacagt     480
aagagaatta tgcagtgctg ccataaccat gagtgataac actgcggcca acttacttct     540
gacaacgatc ggaggaccga aggagctaac cgcttttttg cacaacatgg gggatcatgt     600
aactcgcctt gatcgttggg aaccggagct gaatgaagcc ataccaaacg acgagcgtga     660
caccacgatg cctgtagcaa tggcaacaac gttgcgcaaa ctattaactg gcgaactact     720
tactctagct tcccggcaac aattaataga ctggatggag gcggataaag ttgcaggacc     780
acttctgcgc tcggcccttc cggctggctg gtttattgct gataaatctg gagccggtga     840
gcgtgggtct cgcggtatca ttgcagcact ggggccagat ggtaagccct cccgtatcgt     900
agttatctac acgacgggga gtcaggcaac tatggatgaa cgaaatagac agatcgctga     960
gataggtgcc tcactgatta agcattggta actgtcagac caagtttact catatatact    1020
ttagattgat ttaaaacttc atttttaatt taaaaggatc taggtgaaga tcctttttga    1080
```

```
taatctcatg accaaaatcc cttaacgtga gttttcgttc cactgagcgt cagacccgt      1140 agaaaagatc aaaggatctt cttgagatcc ttttttttctg cgcgtaatct gctgcttgca   1200
aacaaaaaaa ccaccgctac cagcggtggt ttgtttgccg atcaagagc taccaactct     1260 tttttccgaag gtaactggct tcagcagagc gcagatacca aatactgtcc ttctagtgta   1320
gccgtagtta ggccaccact tcaagaactc tgtagcaccg cctacatacc tcgctctgct   1380
aatcctgtta ccagtggctg ctgccagtgg cgataagtcg tgtcttaccg ggttggactc    1440
aagacgatag ttaccggata aggcgcagcg gtcgggctga acggggggtt cgtgcacaca    1500
gcccagcttg gagcgaacga cctacaccga actgagatac ctacagcgtg agcattgaga    1560
aagcgccacg cttcccgaag ggagaaaggc ggacaggtat ccggtaagcg cagggtcgg     1620 aacaggagag cgcacgaggg agcttccagg gggaaacgcc tggtatcttt atagtcctgt    1680
cgggtttcgc cacctctgac ttgagcgtcg attttttgtga tgctcgtcag ggggcggag    1740 cctatggaaa aacgccagca acgcggcctt tttacggttc ctggccttt gctggccttt     1800 tgctcacatg ttctttcctg cgttatcccc tgattctgtg ataaccgta ttaccgcctt     1860 tgagtgagct gataccgctc gccgcagccg aacgaccgag cgcagcgagt cagtgagcga    1920
ggaagcggaa gagcgcccaa tacgcaaacc gcctctcccc gcgcgttggc cgattcatta    1980
atgcagcgga tcaagcttgg atccatcgat gaattcggcg cgccactagt gccgcctgc     2040 agtctagagt cgaccgcaag acccttcctc tatataagga agttcatttc atttggagag    2100
gacacgctcg agtggccacc atggtccgtc ctgtagaaac cccaacccgt gaaatcaaaa    2160
aactcgacgg cctgtgggca ttcagtctgg atcgcgaaaa ctgtggaatt gatcagcgtt    2220
ggtgggaaag cgcgttacaa gaaagccggg caattgctgt gccaggcagt tttaacgatc    2280
agttcgccga tgcagatatt cgtaattatg cgggcaacgt ctggtatcag cgcgaagtct    2340
ttataccgaa aggttgggca ggccagcgta tcgtgctgcg tttcgatgcg gtcactcatt    2400
acggcaaagt gtgggtcaat aatcaggaag tgatggagca tcagggcggc tatacgccat    2460
ttgaagccga tgtcacgccg tatgttattg ccgggaaaag tgtacgtatc accgtttgtg    2520
tgaacaacga actgaactgg cagactatcc cgccgggaat ggtgattacc gacgaaaacg    2580
gcaagaaaaa gcagtcttac ttccatgatt tctttaacta tgccggaatc catcgcagcg    2640
taatgctcta caccacgccg aacacctggg tggacgatat caccgtggtg acgcatgtcg    2700
cgcaagactg taaccacgcg tctgttgact ggcaggtggt ggccaatggt gatgtcagcg    2760
ttgaactgcg tgatgcggat caacaggtgg ttgcaactgg acaaggcact agcgggactt    2820
tgcaagtggt gaatccgcac ctctggcaac cgggtgaagg ttatctctat gaactgtgcg    2880
tcacagccaa aagccagaca gagtgtgata tctacccgct tcgcgtcggc atccggtcag    2940
tggcagtgaa gggcgaacag ttcctgatta ccacaaaacc gttctacttt actggctttg    3000
gtcgtcatga agatgcggac ttgcgtggca aaggattcga taacgtgctg atggtgcacg    3060
accacgcatt aatggactgg attggggcca actcctaccg tacctcgcat tacccttacg    3120
ctgaagagat gctcgactgg gcagatgaac atggcatcgt ggtgattgat gaaactgctg    3180
ctgtcggctt taacctctct ttaggcattg gtttcgaagc gggcaacaag ccgaaagaac    3240
tgtacagcga agaggcagtc aacgggaaa ctcagcaagc gcacttacag gcgattaaag    3300
agctgatagc gcgtgacaaa aaccacccaa gcgtggtgat gtggagtatt gccaacgaac    3360 cggataccg tccgcaaggt gcacgggaat atttcgcgcc actggcggaa gcaacgcgta    3420
aactcgaccc gacgcgtccg atcacctgcg tcaatgtaat gttctgcgac gctcacaccg    3480
```

```
ataccatcag cgatctcttt gatgtgctgt gcctgaaccg ttattacgga tggtatgtcc    3540
aaagcggcga tttggaaacg gcagagaagg tactggaaaa agaacttctg gcctggcagg    3600
agaaactgca tcagccgatt atcatcaccg aatacggcgt ggatacgtta gccgggctgc    3660
actcaatgta caccgacatg tggagtgaag agtatcagtg tgcatggctg gatatgtatc    3720
accgcgtctt tgatcgcgtc agcgccgtcg tcggtgaaca ggtatggaat ttcgccgatt    3780
ttgcgacctc gcaaggcata ttgcgcgttg cggtaacaa gaaagggatc ttcactcgcg    3840
accgcaaacc gaagtcggcg gcttttctgc tgcaaaaacg ctggactggc atgaacttcg    3900
gtgaaaaacc gcagcaggga ggcaaacaat gaatcaacaa ctctcctggc gcaccatcgt    3960
cgctacagcc tcgggaattg ctaccgagct cccgggtacc tgatcatgag taattagctc    4020
gaatttcccc gatcgttcaa acatttggca ataaagtttc ttaagattga atcctgttgc    4080
cggtcttgcg atgattatca tataatttct gttgaattac gttaagcatg taataattaa    4140
catgtaatgc atgacgttat ttatgagatg ggtttttatg attagagtcc cgcaattata    4200
catttaatac gcgatagaaa acaaaatata gcgcgcaaac taggataaat tatcgcgcgc    4260
ggtgtcatct atgttactag atcgggaatt agatctgct                          4299

<210> SEQ ID NO 18
<211> LENGTH: 37
<212> TYPE: DNA
<213> ORGANISM: Artificial Sequence
<220> FEATURE:
<223> OTHER INFORMATION: derived from Solanum tuberosum

<400> SEQUENCE: 18
actagtttct agccaccaga tttgaccaaa ctctaga                                  37

<210> SEQ ID NO 19
<211> LENGTH: 36
<212> TYPE: DNA
<213> ORGANISM: Artificial Sequence
<220> FEATURE:
<223> OTHER INFORMATION: derived from Petroselinum crispum

<400> SEQUENCE: 19
actagtcagc caccaaagag gacccagaat tctaga                                   36

<210> SEQ ID NO 20
<211> LENGTH: 43
<212> TYPE: DNA
<213> ORGANISM: Artificial Sequence
<220> FEATURE:
<223> OTHER INFORMATION: derived from Petroselinum crispum

<400> SEQUENCE: 20
actagttaca attcaaacat tgttcaaaca aggaacctct aga                           43

<210> SEQ ID NO 21
<211> LENGTH: 42
<212> TYPE: DNA
<213> ORGANISM: Artificial Sequence
<220> FEATURE:
<223> OTHER INFORMATION: derived from Petroselinum crispum

<400> SEQUENCE: 21
actagtagtt gaaattcaat aagttgaaat tcaatatcta ga                            42

<210> SEQ ID NO 22
<211> LENGTH: 42
<212> TYPE: DNA
```

```
<213> ORGANISM: Artificial Sequence
<220> FEATURE:
<223> OTHER INFORMATION: derived from Petroselinum crispum

<400> SEQUENCE: 22
actagtcaca cttaatttga ccgagtaaca ttcgcctcta ga                        42

<210> SEQ ID NO 23
<211> LENGTH: 41
<212> TYPE: DNA
<213> ORGANISM: Artificial Sequence
<220> FEATURE:
<223> OTHER INFORMATION: derived from Petroselinum crispum

<400> SEQUENCE: 23
actagtttat tcagccatca aagttgacca ataattctag a                         41

<210> SEQ ID NO 24
<211> LENGTH: 10
<212> TYPE: DNA
<213> ORGANISM: Solanum tuberosum

<400> SEQUENCE: 24
agccaccaga                                                            10

<210> SEQ ID NO 25
<211> LENGTH: 36
<212> TYPE: DNA
<213> ORGANISM: Artificial Sequence
<220> FEATURE:
<223> OTHER INFORMATION: derived from Triticum aestivum

<400> SEQUENCE: 25
actagtggat tgacttgacc gtcatcggct tctaga                               36

<210> SEQ ID NO 26
<211> LENGTH: 39
<212> TYPE: DNA
<213> ORGANISM: Artificial Sequence
<220> FEATURE:
<223> OTHER INFORMATION: derived from Petroselinum crispum

<400> SEQUENCE: 26
actagttcaa tatgtcaatg gtcaacattc aactctaga                            39

<210> SEQ ID NO 27
<211> LENGTH: 38
<212> TYPE: DNA
<213> ORGANISM: Artificial Sequence
<220> FEATURE:
<223> OTHER INFORMATION: 2s102

<400> SEQUENCE: 27
aatttgttga cagccttttg gtcaaagcac tgacttgg                             38

<210> SEQ ID NO 28
<211> LENGTH: 26
<212> TYPE: DNA
<213> ORGANISM: Artificial Sequence
<220> FEATURE:
<223> OTHER INFORMATION: C109

<400> SEQUENCE: 28
caatatgtca atggtcaaca ttcaac                                          26

<210> SEQ ID NO 29
```

```
<211> LENGTH: 26
<212> TYPE: DNA
<213> ORGANISM: Artificial Sequence
<220> FEATURE:
<223> OTHER INFORMATION: 17s102

<400> SEQUENCE: 29
tcaattgtca atggtcaaca ttcaac                                          26

<210> SEQ ID NO 30
<211> LENGTH: 26
<212> TYPE: DNA
<213> ORGANISM: Artificial Sequence
<220> FEATURE:
<223> OTHER INFORMATION: 15s102

<400> SEQUENCE: 30
tcaatatgta atggtcaaca ttcaac                                          26

<210> SEQ ID NO 31
<211> LENGTH: 27
<212> TYPE: DNA
<213> ORGANISM: Artificial Sequence
<220> FEATURE:
<223> OTHER INFORMATION: 18s102

<400> SEQUENCE: 31
gttgaatgtt gaccattgac atattga                                         27

<210> SEQ ID NO 32
<211> LENGTH: 27
<212> TYPE: DNA
<213> ORGANISM: Artificial Sequence
<220> FEATURE:
<223> OTHER INFORMATION: B109 / H149

<400> SEQUENCE: 32
tcaatatgtc aatggtcaac attcaac                                         27

<210> SEQ ID NO 33
<211> LENGTH: 20
<212> TYPE: DNA
<213> ORGANISM: Artificial Sequence
<220> FEATURE:
<223> OTHER INFORMATION: C175

<400> SEQUENCE: 33
tcaatatgtc aatggtcaac                                                 20

<210> SEQ ID NO 34
<211> LENGTH: 14
<212> TYPE: DNA
<213> ORGANISM: Artificial Sequence
<220> FEATURE:
<223> OTHER INFORMATION: D175

<400> SEQUENCE: 34
tgtcaatggt caac                                                       14

<210> SEQ ID NO 35
<211> LENGTH: 210
<212> TYPE: DNA
<213> ORGANISM: Artificial Sequence
<220> FEATURE:
<223> OTHER INFORMATION: Cut-out of the polylinker of the vector ms23
      (17)

<400> SEQUENCE: 35
```

```
ggaagcggaa gagcgcccaa tacgcaaacc gcctctcccc gcgcgttggc cgattcatta      60
atgcagcgga tcaagcttgg atccatcgat gaattcggcg cgccactagt gccggcctgc     120
agtctagagt cgaccgcaag acccttcctc tatataagga agttcatttc atttggagag     180
gacacgctcg agtggccacc atggtccgtc                                      210
```

CHIMERIC PROMOTERS CAPABLE OF MEDIATING GENE EXPRESSION IN PLANTS UPON PATHOGEN INFECTION AND USES THEREOF

CROSS-REFERENCE TO RELATED APPLICATIONS

This application is a continuation-in-part of patent application Ser. No. 09/831,272, filed Aug. 13, 2001, entitled CHIMERIC PROMOTERS CAPABLE OF MEDIATING GENE EXPRESSION IN PLANTS UPON PATHOGEN INFECTION AND USES THEREOF, and allowed as U.S. Pat. No. 8,013,138 on Sep. 6, 2011, which is a National Stage Entry of PCT/EP99/08710, filed Nov. 12, 1999, entitled CHIMERIC PROMOTERS CAPABLE OF MEDIATING GENE EXPRESSION IN PLANTS UPON PATHOGEN INFECTION AND USES THEREOF, both of which are incorporated herein in their entirety.

FIELD OF THE INVENTION

The present invention relates to synthetic promoters capable of mediating gene expression in plants upon pathogen infection. The present invention also relates to recombinant genes and vectors comprising said chimeric promoters as well as to host cells transformed with such chimeric promoters, recombinant genes or vectors. The present invention additionally relates to diagnostic compositions and kits comprising such chimeric promoters, recombinant genes, vectors or cells.

The present invention also relates to methods for the identification of compounds being capable of activating or inhibiting genes that are specifically expressed in plants upon pathogen infection employing the above described means. Furthermore, the present invention relates to transgenic plant cells, plant tissue and plants containing the above-described chimeric promoters, recombinant genes and vectors as well as to the use of the aforementioned chimeric promoters, recombinant genes, vectors and/or compounds identified by the method of the invention in plant cell and tissue culture, plant breeding and/or agriculture.

BACKGROUND OF THE INVENTION

The engineering of disease resistance in crops is a major focus of plant biotechnology. One of the most promising approaches to this problem is to engineer defense reactions that are closely related to natural defense mechanisms such as hypersensitive cell death at infection sites, where the cells immediately surrounding an infection site die in order to prevent further spread of the pathogen (Strittmatter, Bio/Technology 13(1995), 1085-1089). The controlled generation of highly localized necrotic lesions depends, however, on restricting any cytotoxic activity to the infection sites. This therefore requires promoters that are rapidly and locally responsive to pathogen attack but that also show negligible activity in uninfected tissues.

Initial attempts using large promoter fragments from pathogenesis-related genes such as prp1-1 have suffered from the disadvantage that it is difficult to isolate a promoter that is totally pathogen specific with substantially no activity in non-infected tissue (Strittmatter, 1995). It seems likely therefore that very few, if any, naturally occurring promoters will be suitable for this purpose.

Recent advances in the detailed study of defense related genes have identified a number of functionally defined cis-acting regulatory DNA elements within pathogen inducible promoters (Korfhage, The Plant Cell 6 (1994), 695-708, Raventos, Plant J. 7(1995), 147-155, Rushton, EMBO J. 15 (1996), 5690-5700). A number of cis-acting elements that are necessary for the response to pathogens have been defined. These include Boxes P and L from the parsley PAL genes (Logemann, Proc. Natl. Acad. Sci. USA 92(1995), 5905-5909), Boxes H and G from soybean PAL and 4CL (Loake, Proc. Natl. Acad. Sci. USA 89 (1992), 9230-9234), together with a number of less well defined elements. However, while it was shown for a number of such cis-acting elements that they are necessary for elicitor inducibility it was not known whether these elements are sufficient to direct pathogen-induced expression in plant cells and plants on their own. Recently, it has only been shown for the Box W1 from parsley (Rushton, EMBO J. 15(1996), 5690-5700) and ERE from the maize Prms (Raventos, Plant J. 7(1995), 147-155) that four copies of these elements alone are sufficient to direct elicitor responsive expression to some extent in transient gene expression assays. However, inducibility and background level of expression of the constructs investigated in Rushton, 1996 and Raventos, 1995 greatly varied and at best an about 10-fold induction of reporter gene expression was observed that may not be sufficient to supply the above-described biotechnological needs. Accordingly, it was unclear whether these or any other cis-acting elements may be useful to specifically suppress or confer local gene expression in plants upon pathogen infection.

Thus, the technical problem of the present invention is to provide promoters that are rapidly and locally responsive to pathogen attack but show negligible activity in uninfected parts of the plant and that can be used for engineering of disease resistant crops.

The solution to this technical problem is achieved by providing the embodiments characterized in the claims.

SUMMARY OF THE INVENTION

Accordingly, the invention relates to a chimeric promoter capable of mediating local gene expression in plants upon pathogen infection comprising
(i) at least one cis-acting element sufficient to direct elicitor-specific expression comprising the nucleotide sequence of any one of SEQ ID NOS: 3 to 16, and
(ii) a minimal promoter.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 7 shows elicitor inducibility of Box E17 depending on the distance to the 35S minimal promoter, as illustrated in FIG. 6. FIG. 8 shows expression characteristics of transgenic plants transformed with reporter gene constructs comprising chimeric promoters with tetramers of some cis-elements of the present invention. For comparison the GCC-Box element is included (see Example 1). The background expression levels are quantified as being low (barely detectable background expression), medium (visible background expression but induction by pathogens is clearly visible over the background) or very high (extremely high expression such that induction by pathogens is difficult to detect). A minus indicates no detectable expression, a plus indicates inducible expression and "nt" not tested.

DETAILED DESCRIPTION OF THE INVENTION

Figure 1:
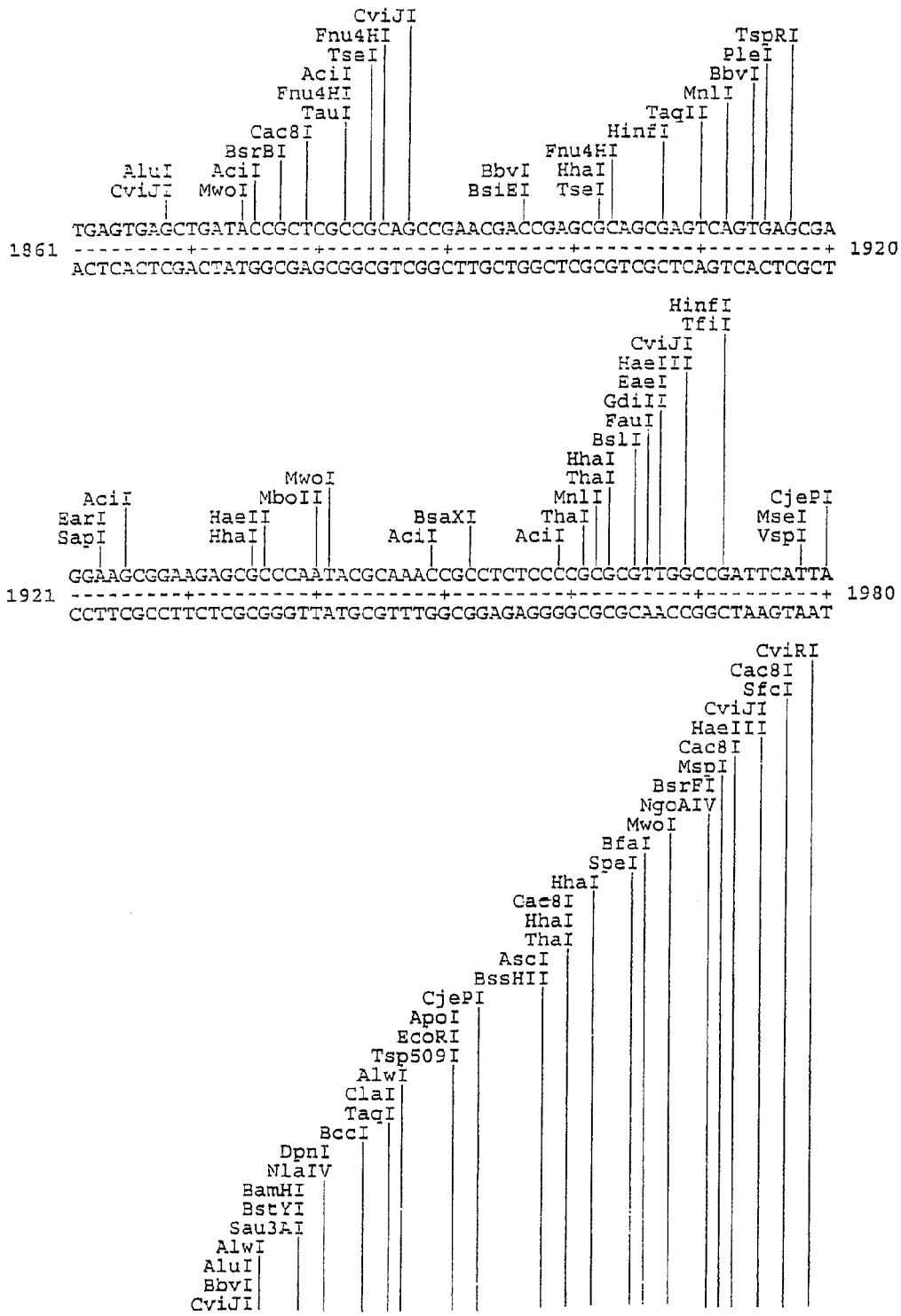
FIG. 1 shows a restriction map of the plasmid ms23 (Sprenger, 1997) (SEQ ID NO: 17)

The term "capable of mediating local gene expression in plants upon pathogen infection" as used herein means that said promoter is capable of controlling the expression of a heterologous DNA sequence at infection sites, analogous or closely related to the controlled expression of pathogen related genes which are involved in the natural resistance in most incompatible host/pathogen interactions, such as the hypersensitive cell death at infection sites of a part of a plant. Thus, the chimeric promoter of the invention is characterized by its capability of mediating localized transcriptional activation selectively in response to pathogen attack or in response to stimuli that mimic pathogen attack such as elicitors prepared from, e.g., pathogens such as fungi or bacteria or derivatives thereof. The transcriptional activation by the chimeric promoter of the invention may also occur in cells surrounding the actual infection site due to cell-cell interactions. The chimeric promoter of the invention may advantageously not or only to a small extent be inducible upon other stimuli such as abiotic stress. Preferably, the induction from the chimeric promoter upon pathogen attack or elicitor treatment is at least about 10-fold higher, preferably 20-fold higher and particularly 30-fold higher than its activation, if any, by abiotic stress.

However, the expression specificity conferred by the chimeric promoters of the invention may not be limited to local gene expression due to pathogens, for example, they may be combined with further regulatory sequences that provide for tissue specific gene expression. The particular expression pattern may also depend on the plant/vector system employed. However, expression of heterologous DNA sequences driven by the chimeric promoters of the invention predominantly occurs upon pathogen infection or treatment with a corresponding elicitor unless certain elements of the invention were taken and designed by the person skilled in the art to control the expression of a heterologous DNA sequence in certain cell types.

The term "cis-acting element sufficient to direct elicitor-specific expression" denotes a short stretch of a DNA preferably between 6 and 35 nucleotides in length that when combined with a minimal promoter such as the CaMV 35S minimal promoter (positions −46 to +8) is capable of directing high level elicitor-specific expression of a heterologous DNA sequence. Preferably, said elicitor is a fungal elicitor that can be prepared by conventional means; see, e.g., Ayers, Plant Physiol. 57(1976), 760-765; Grosskopf, J. Plant Physiol. 138 (1991), 741-746; Kombrink, Plant Physiol. 81(1986), 216-221; West, Naturwissenschaften 68(1981), 447-457.

The term "minimal promoter", within the meaning of the present invention refers to nucleotide sequences necessary for transcription initiation, i.e. RNA polymerase binding, and may also include, for example, the TATA box.

The term "pathogen" includes, for example, bacteria, viruses, fungi and protozoa as well as elicitors prepared therefrom.

In accordance with the present invention a number of cis-acting elements have been identified that alone are sufficient to direct high level fungal elicitor-specific expression and that can be used to construct novel synthetic promoters that for the first time meet the requirements for engineering disease resistant crops.

Studies that have been performed in accordance with the present invention employed a homologous transient expression system that uses parsley (*Petroselinum crispum*) protoplasts derived from cultured cells. This system is one of very few where the protoplasts respond to fungal elicitor molecules in an almost identical way to cells in the intact plant (Dangl, EMBO J. 6(1987), 2551-2556; Hahlbrock, Proc. Natl. Acad. Sci. USA 92 (1995), 4150-4157). This allows the study of elicitor-responsive cis-acting elements, something that is difficult in many other experimental systems.

Eleven cis-acting elicitor-responsive elements (SEQ ID NOS: 3 to 13) were identified in accordance with the present invention. Monomers and multimers of each element were constructed in addition to synthetic promoters consisting of two or more of these elements in combination. Each construct was synthesized with either BamHI ends or with a SpeI site at the 5' end and an XbaI site at the 3' end and then cloned into the corresponding restriction site in front of a minimal CaMV 35S promoter (−46 to +8) in the vector MS23-pBT10-GUS (Sprenger, Ph.D. thesis, University of Köln, Köln, Germany (1997); see FIG. 1 (SEQ ID NO: 17) and FIG. 2). The distance between the insertion site and the TATA Box varied between 25 and 70 bp depending on the insertion site employed and only slight differences, if any, were seen when the same element was inserted into different restriction sites.

Additionally, the cis-acting elicitor-responsive element Box E17(SEQ ID NO: 15) was identified in accordance with the present invention. Synthetic promoters were constructed comprising a monomer, a dimer or the reverse complement of this element. Various distances between 5 and 131 bp from the inserted Box E17 to the minimal promoter were tested using monomers and dimers (see Example 7). Usable inducibility in the sense of the present invention was obtained for distances of at least 12 bp, and optimal inducibility for distances of 40 to 60 bp to the 5'-end of the minimal promoter. Another cis-acting element of the present invention, the 21 bp long 3'-fragment of Box E17 (SEQ ID NO: 16) confers a similar elicitor-responsiveness as compared to Box E17(see Example 6).

The experiments performed in accordance with the present invention demonstrate that the cis-acting elements direct pathogen-induced expression in vivo, being active as monomers, multimers and in combination with each other within synthetic promoters. They therefore meet the biotechnological requirements for the engineering of disease resistance.

In accordance with the present invention these novel chimeric promoters cloned in front of the GUS coding region and the resulting chimeric genes were introduced by means of vacuum infiltration mediated gene transfer into *Arabidopsis* plants; see Example 8. The expression pattern observed in the transgenic plants containing the GUS marker gene under the control of the chimeric promoter of the invention revealed expression in tissue infected by bacterial (*Pseudomonas syringae*) as well as by fungal pathogens (*Peronospora parasitica*), whereas local expression in wounded tissues seems to be inactive.

The chimeric promoter of the invention may be preferably comprised only of the above defined cis-acting elements and a minimal promoter. As will be discussed below, other regulatory sequences may be added or present dependent on the intended use of the chimeric promoter of the invention. However, preferably the chimeric promoter of the invention lacks elements that interfere with the elicitor specific expression and/or which are responsible for the non-selective expression of the promoter the cis-acting element of the invention was derived from.

To obtain possible expression in all tissues of a transgenic plant, the minimal regulatory sequences of constitutive promoters are often used, such as the 35 S promoter of CaMV (Odell, Nature 313(1985), 810-812) or promoters of the polyubiquitin genes of maize (Christensen, Plant Mol. Biol. 18(1982), 675-689). It is also immediately evident to the person skilled in the art that further regulatory elements may be added to the chimeric sequences of the invention. For example, transcriptional enhancers and/or sequences which allow for further induced expression of the chimeric promoter of the invention may be employed Enhancer sequences functional in plants include, for example, ocs-element (Ellis, EMBO J. 6(1987), 3203-3208); the family of ACGT-elements (hex-motif, G-box as 1-element) (Williams, Plant Cell 4 (1992), 485-496) and the cyt-1 element (Neuteboom, Plant J. 4(1993), 525-534). In order to achieve expression in specific tissues of a transgenic plant it is possible to use tissue specific promoters (see, e.g., Stockhaus, EMBO J. 8 (1989), 2245-2251). Known are also promoters which are specifically active in tubers of potatoes or in seeds of different plants species, such as maize, Vicia, wheat, barley etc. Furthermore, the chemically inducible Tet-system may be employed (Gatz, Mol. Gen. Genet. 227(1991); 229-237). Further suitable promoters are known to the person skilled in the art and are described, e.g., in Ward (Plant Mol. Biol. 22(1993), 361-366).

Preferably, the chimeric promoter of the invention further comprises a cis-acting element having the nucleotide sequence of SEQ ID NO: 1 or 2; see Example 5.

In a particularly preferred embodiment of the invention the chimeric promoter comprises homo- and/or hetero-multimeric forms of said cis-acting element(s); see also the appended Example 5. Preferably, said multimeric form is a dimer or tetramer. Particularly preferred are those combinations of cis-acting elements that are described in Example 5 and which combination provide for an at least 20-fold, preferably at least 30-fold and particularly preferred at least about 50-fold induction.

In a preferred embodiment of the chimeric promoter of the invention the minimal promoter is derived from the CaMV35S promoter, CHS promoter, PR1 promoter, or hcbt2 promoter. However, other minimal promoters from other sources may be employed as well.

In a further preferred embodiment of the chimeric promoter of the invention, the distance between said cis-acting element and said minimal promoter is 12 to 300 base pairs, more preferably 25 to 70 base pairs, and most preferably 40 to 60 base pairs. In addition or alternatively, a spacer region preferably composed of 4 to 10 base pairs separates at least two of said cis-acting elements in the chimeric promoter. Likewise, it is preferred that at least two of said multimeric forms in the chimeric promoter described above are separated by a spacer of between about 50 to 1000 base pairs.

In a particularly preferred embodiment of the chimeric promoter of the invention the induction of gene expression upon elicitor treatment or pathogen infection is at least 15-fold. As discussed before, the cis-acting elements so far investigated in the prior art only provided for induction upon elicitor treatment of about 10-fold. However, a 10-fold induction of a recombinant gene encoding, e.g., an anti-viral protein may not be sufficient to rapidly and efficiently combat against the pathogen. The present invention provides several cis-acting elements that are capable of inducing high level expression of a given DNA sequence up to 400-fold induction; see, e.g., Example 1. Furthermore, the invention demonstrates that the combination of otherwise weak cis-acting elements can provide for a substantial increase of the overall inducibility of the chimeric promoter; see Example 5. Thus, the present invention for the first time provides a generally applicable method for how to construct and use chimeric promoters in the field of plant biotechnology. As will be noted from the appended Examples, the background value of the chimeric promoters of the invention may vary to a certain extent. The person skilled in the art therefore may employ different chimeric promoters with different background levels and inducibility depending on the intended use. For example, if the approach of coat protein-mediated protection against virus infection is used the chimeric promoter employed may have high background level expression that would not harm the plant and which upon viral infection would increase at high levels such that resistance to the virus can be obtained. The same rational would apply to, e.g., an antisense or ribozyme mediated protection or the engineering of resistance to fungal pathogens by the expression of antifungal proteins etc. On the other hand, where the generation of race-specific resistant genes and artificial generation of hypersensitive cell death is intended, preferably a chimeric promoter is used that has low or substantially no background activity and that only upon pathogen attack is activated to an extent that sufficient level of toxic protein is made so as to cause the cell to die. The selection of the appropriate chimeric promoter of the invention depending on its use is well within the skill of the person skilled in the art.

Examples of the different possible applications of the chimeric promoter according to the invention as well as its cis-acting elements will be described in detail in the following.

Hence, in a further embodiment, the present invention relates to a recombinant gene comprising the above-described chimeric promoter. Preferably, the recombinant gene is configured such that the chimeric promoter is operatively linked to a heterologous DNA sequence.

The term "heterologous" with respect to the DNA sequence being operatively linked to the chimeric promoter of the invention means that said DNA sequence is not naturally linked to the chimeric promoter of the invention.

The term "operably linked" refers to a juxtaposition wherein the components so described are in a relationship permitting them to function in their intended manner. The chimeric promoter "operably linked" to a heterologous DNA sequence is ligated in such a way that expression of a coding sequence is achieved under conditions compatible with the control sequences. Expression comprises transcription of the heterologous DNA sequence preferably into a translatable mRNA. Regulatory elements ensuring expression in eukaryotic, i.e. plant cells are well known to those skilled in the art. In the case of eukaryotic cells they comprise optionally poly-A signals ensuring termination of transcription and stabilization of the transcript, for example, those of the 35S RNA from Cauliflower Mosaic Virus (CaMV) and the Nopaline Synthase gene from *Agrobacterium tumefaciens*. Additional regulatory elements may include transcriptional as well as translational enhancers. A plant translational enhancer often used is the CAMV omega sequences, the inclusion of an intron (Intron-1 from the Shrunken gene of maize, for example) has been shown to increase expression levels by up to 100-fold. (Mait, Transgenic Research 6(1997), 143-156; Ni, Plant Journal 7 (1995), 661-676). In this respect, it should be noted that in one embodiment of the recombinant gene of the invention at least one of said cis-acting elements is located in the 5'- or 3-untranslated region or in an intron of the recombinant gene.

In a preferred embodiment of the recombinant gene of the invention said heterologous DNA sequence encodes a (poly) peptide, cytotoxic protein, antibody, antisense RNA, sense RNA, ribozyme, transcription factor, protease, nuclease, lipase, or polymerase.

The recombinant gene of the invention can be used alone or as part of a vector to express heterologous DNA sequences, which, e.g., encode proteins for, e.g., the control of disease resistance or diagnostics of pathogen inducible or related gene expression. The recombinant gene or vector containing the DNA sequence encoding an RNA or a protein of interest is introduced into the cells which in turn produce the RNA or protein of interest. For example, the chimeric promoter of the invention can be operatively linked to DNA sequences encoding Barnase for use in the production of localized cell death in plants upon pathogen attack.

On the other hand, said protein can be a scorable marker, e.g., luciferase, green fluorescent protein or β-galactosidase. This embodiment is particularly useful for simple and rapid screening methods for compounds and substances described herein below capable of modulating pathogene specific or elicitor inducible gene expression. For example, transgenic plant cells can be cultured in the presence and absence of a candidate compound in order to determine whether the compound affects the expression of genes which are under the control of chimeric promoters of the invention, which can be measured, e.g., by monitoring the expression of the above-mentioned marker. It is also immediately evident to those skilled in the art that other marker genes may be employed as well, encoding, for example, a selectable marker which provides for the direct selection of compounds which induce or inhibit the expression of said marker.

The chimeric promoters of the invention may also be used in methods of antisense approaches. The antisense RNA may be a short (generally at least 10, preferably at least 14 nucleotides, and optionally up to 100 or more nucleotides) nucleotide sequence formulated to be complementary to a portion of a specific mRNA sequence and/or DNA sequence of the gene of interest. Standard methods relating to antisense technology have been described; see, e.g., Klann, Plant Physiol. 112(1996), 1321-1330. Following transcription of the DNA sequence into antisense RNA, the antisense RNA binds to its target sequence within a cell, thereby inhibiting translation of the mRNA and down-regulating expression of the protein encoded by the mRNA.

Furthermore, appropriate ribozymes can be employed (see, e.g., EP-A1 0 291 533, EP-A1 0 321 201, EP-A2 0 360 257) which specifically cleave the (pre)-mRNA of a target gene. Selection of appropriate target sites and corresponding ribozymes can be done as described for example in Steinecke, Ribozymes, Methods in Cell Biology 50, Galbraith, eds Academic Press, Inc. (1995), 449-460. Further applications of the chimeric promoter are evident to the person skilled in the art and can be derived from the literature, e.g., Strittmatter and Wegener, Zeitschrift fair Naturforschung 48c (1993), 673-688; Kahl, J. Microbiol. Biotechnol. 11 (1995), 449-460 and references cited therein.

Said transcription factor can for example be a master regulatory factor that controls the expression of a cascade of genes involved in pathogen defense of the plant (Grotewold, Plant Cell 10(1998), 721-740; Rushton and Somssich, Curr. Opin. Plant Biol. 1(1998), 311-315). Alternatively, it can be a hybrid transcription factor containing a DNA-binding domain (e.g. of GAL4 or of the bacteriophage 434) and an activator domain (e.g. of VP16 or of any functional plant activator domain), which, when expressed in transgenic plants containing an antisense target gene under the control of a synthetic promoter containing the appropriate cis-acting element recognizing the hybrid factor, leads to specific repression (knock-out) of the desired endogenous gene function (Wilde, Plant Mol. Biol. 24(1994), 381-388; Guyer, Genetics 149(1998), 633-639).

Suitable lipases comprise for example phospholipases, e.g., C or $A_2$ type phospholipases (Scherer, Plant Growth regulation 18(1996), 125-133). Lipases are capable of releasing free fatty acids from membrane lipids, wherein these fatty acids can function as signal transducers by which general cellular defense reactions are elicited. The growing importance of free fatty acids in pathogen-defense is documented, e.g., in Scherer (1996), Roy (Plant Sci. 107(1995), 17-25 and references cited therein) and Tavernier (Plant Sci. 104 (1995), 117-125).

Nucleases, i.e. RNases and DNases, may also be employed, of which Barnase is one candidate among others. The use of proteases in the context of this embodiment may apply to cytotoxic effects.

A signal amplification system may be constructed using polymerases. In a two-step model, an elicitor-induced polymerase, e.g., SP6-, T7- or T3-RNA polymerase, can transcribe a second recombinant gene which is controlled by a promoter to which the polymerase is highly specific. The second gene may encode for example a cytotoxic protein which is then expressed in an amplified way. A plant system based on T7-RNA polymerase was described by McBride (Proc. Natl. Acad. Sci. USA 91(1994), 7301-7305).

Cytotoxic proteins comprise, for example, plant RIPs (ribosome inactivating proteins; (Stripe, Bio/Technology 10 (1992), 405-412), defensins (Broekaert, Plant Physiol. 108 (1995), 1353-1358), Bt toxin, α-amylase inhibitor, T4-lysozyme, avirulence gene products, or enzymes such as glucose oxidase which generate reactive oxygen species (Shah, Trends Biotechnol. 13(1995), 362-368; Shah, Curr. Opin. Biotech. 8 (1997), 208-214; Beachy, Curr. Opin. Biotech. 8(1997), 215-220; Cornelissen, Plant Physiol. 101(1993), 709-712; Estruch, Nucleic Acids Res. 22(1994), 3983-3989).

It is in principle possible to modify the coding sequence in such a way that the protein is located in any desired compartment of the plant cell. These include the nucleus, endoplasmatic reticulum, the vacuole, the mitochondria, the plastids, the apoplast, the cytoplasm etc. Methods how to carry out this modifications and signal sequences ensuring localization in a desired compartment are well known to the person skilled in the art. (Görlich, Science 271(1996), 1513-1518; Hicks, Plant Physiol. 107 (1995), 1055-1058; Rachubinski, Cell 83(1995), 525-528; Schatz, Science 271(1996), 1519-1526; Schnell, Cell 83(1995), 521-524; Verner, Science 24(1988), 1307-1313; Vitale, BioEssays 14(1992), 151-160).

The present invention also relates to vectors, particularly plasmids, cosmids, viruses and bacteriophages used conventionally in genetic engineering that comprise a chimeric promoter or a recombinant gene of the invention. Preferably, said vector is a plant expression vector, preferably further comprising a selection marker for plants. For example of suitable selector markers, see supra. Methods which are well known to those skilled in the art can be used to construct recombinant vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the chimeric promoters and recombinant genes of the invention can be reconstituted into liposomes for delivery to target cells.

Advantageously, the above-described vectors of the invention comprise a selectable and/or scorable marker. Selectable marker genes useful for the selection of transformed plant cells, callus, plant tissue and plants are well known to those skilled in the art and comprise, for example, antimetabolite resistance as the basis of selection for dhfr, which confers resistance to methotrexate (Reiss, Plant Physiol. (Life Sci. Adv.) 13(1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32(1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59(1995), 2336-2338).

Useful scorable marker are also known to those skilled in the art and are commercially available. Advantageously, said marker is a gene encoding luciferase (Giacomin, Pl. Sci. 116(1996), 59-72; Scikantha, J. Bact. 178 (1996), 121), green fluorescent protein (Gerdes, FEBS Lett. 389(1996), 44-47) or β-glucuronidase (Jefferson, EMBO J. 6(1987), 3901-3907). This embodiment is particularly useful for simple and rapid screening of cells, tissues and plants containing a vector of the invention.

The present invention furthermore relates to host cells comprising a chimeric promoter, recombinant gene or a vector according to the invention wherein the chimeric promoter is foreign to the host cell.

By "foreign" it is meant that the chimeric promoter is either heterologous with respect to the host cell, this means derived from a cell or organism with a different genomic background, or is homologous with respect to the host cell but located in a different genomic environment than the naturally occurring counterpart of said cis-acting element. This means that, if the cis-acting element is homologous with respect to the host cell, it is not located in its natural location in the genome of said host cell, in particular it is surrounded by different genes. The vector or recombinant gene according to the invention which is present in the host cell may either be integrated into the genome of the host cell or it may be maintained in some form extrachromosomally. In this respect, it is also to be understood that the chimeric promoter or recombinant gene of the invention can be used to restore or create a mutant gene via homologous recombination (Paszkowski (ed.), Homologous Recombination and Gene Silencing in Plants. Kluwer Academic Publishers (1994)). The host cell can be any prokaryotic or eukaryotic cell, such as bacterial, insect, fungal, plant or animal cells. Preferred cells are plant cells.

In a further preferred embodiment, the present invention provides for a method for the production of transgenic plants, plant cells or plant tissue comprising the introduction of a chimeric promoter, recombinant gene or vector of the invention into the genome of said plant, plant cell or plant tissue. For the expression of the heterologous DNA sequence under the control of the chimeric promoter according to the invention in plant cells, further regulatory sequences such as poly A tail may be fused, preferably 3' to the heterologous DNA sequence, see also supra. Further possibilities might be to add Matrix Attachment Sites at the borders of the transgene to act as "delimiters" and insulate against methylation spread from nearby heterochromatic sequences.

Methods for the introduction of foreign genes into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, vacuum infiltration, biolistic methods like particle bombardment, pollen-mediated transformation, plant RNA virus-mediated transformation, liposome-mediated transformation, transformation using wounded or enzyme-degraded immature embryos, or wounded or enzyme-degraded embryogenic callus and other methods known in the art. The vectors used in the method of the invention may contain further functional elements, for example "left border"- and "right border"-sequences of the T-DNA of *Agrobacterium* which allow stable integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example cotransformation (Lyznik, Plant Mol. Biol. 13(1989), 151-161; Peng, Plant Mol. Biol. 27(1995), 91-104) and/or by using systems which utilize enzymes capable of promoting homologous recombination in plants (see, e.g., WO97/08331; Bayley, Plant Mol. Biol. 18 (1992), 353-361); Lloyd, Mol. Gen. Genet. 242 (1994), 653-657; Maeser, Mol.

Gen. Genet. 230(1991), 170-176; Onouchi, Nucl. Acids Res. 19 (1991), 6373-6378). Methods for the preparation of appropriate vectors are described by, e.g., Sambrook (Molecular Cloning; A Laboratory Manual, 2 nd Edition (1989), Cold Spring Harbor Laboratory Press, Cold Spring Harbor, N.Y.).

Suitable strains of *Agrobacterium tumefaciens* and vectors as well as transformation of *Agrobacteria* and appropriate growth and selection media are well known to those skilled in the art and are described in the prior art (GV3101 (pMK90RK), Koncz, Mol. Gen. Genet. 20(1986), 383-396; C58C1 (pGV 3850kan), Deblaere, Nucl. Acid Res. 13 (1985), 4777; Bevan, Nucleic. Acid Res. 12 (1984), 8711; Koncz, Proc. Natl. Acad. Sci. USA 86(1989), 8467-8471; Koncz, Plant Mol. Biol. 20(1992), 963-976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1-22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1-46; An, EMBO J. 4(1985), 277-287). Although the use of *Agrobacterium tumefaciens* is preferred in the method of the invention, other *Agrobacterium* strains, such as *Agrobacterium rhizogenes*, may be used, for example if a phenotype conferred by said strain is desired.

Methods for the transformation using biolistic methods are well known to the person skilled in the art; see, e.g., Wan, Plant Physiol. 104(1994), 37-48; Vasil, Bio/Technology 11(1993), 1553-1558 and Christou (1996) Trends in Plant Science 1, 423-431. Microinjection can be performed as described in Potrykus and Spangenberg (eds.), Gene Transfer To Plants. Springer Verlag, Berlin, N.Y. (1995).

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc.

The resulting transformed plant cell can then be used to regenerate a transformed plant in a manner known by a skilled person.

Alternatively, a plant cell can be used and modified such that said plant cell expresses an endogenous gene under the control of the chimeric promoter. The introduction of the chimeric promoter of the invention which does not naturally control the expression of a given gene or genomic sequences using, e.g., gene targeting vectors can be done according to standard methods, see supra and, e.g., Hayashi, Science 258 (1992), 1350-1353; Fritze and Walden, Gene activation by T-DNA tagging. In Methods in Molecular biology 44(Gartland, K. M. A. and Davey, M. R., eds). Totowa: Human Press (1995), 281-294) or transposon tagging (Chandlee, Physiologia Plantarum 78(1990), 105-115).

In general, the plants which can be modified according to the invention can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc.

Thus, the present invention relates also to transgenic plant cells comprising, preferably stably integrated into the genome, a chimeric promoter, a recombinant gene or vector according to the invention or obtainable by the above-described method.

Furthermore, the present invention also relates to transgenic plants and plant tissue comprising the above-described transgenic plant cells or obtainable by the above-described method. These plants may show, for example, increased disease resistance.

In a preferred embodiment of the invention, the transgenic plant upon the presence of the chimeric promoter or the recombinant gene of the invention attained resistance or improved resistance against a pathogen the corresponding wild-type plant was susceptible to.

The term "resistance" covers the range of protection from a delay to complete inhibition of disease development. Examples for pathogens of importance comprise *Phytophthora infestans*, the causal agent of potato late blight disease, *Phytophthora sojae*, root rot pathogen of soybean, *Peronospora parasitica* (downy mildew), *Magnaporthe grisea*, causal agent of rice blast disease, *Erysiphe* spp (powdery mildew), *Pseudomonas syringae* (agent of bacterial blight), *Erwinia amylovora*(fire blight disease), *Erwinia carotovora* (soft rot), *Botrytis cinerea* (downy mildew of grape), *Rhizoctonia solani* and *Pythium debaryanum*(agents of seedling blight or damping off disease).

In yet another aspect the invention also relates to harvestable parts and to propagation material of the transgenic plants according to the invention which contain transgenic plant cells described above. Harvestable parts can be in principle any useful part of a plant, for example, leaves, stems, fruit, seeds, roots etc. Propagation material includes, for example, seeds, fruits, cuttings, seedlings, tubers, rootstocks etc.

As discussed above, novel cis-acting elements have been identified in accordance with the present invention that are capable of conferring elicitor inducible or pathogen specific gene expression in plant cells and plants. Therefore, the present invention also relates to cis-acting elements as defined above or multimeric forms of any one of those as discussed hereinbefore.

Due to the tight regulation of the chimeric promoters of the invention it is evident that they are particularly suited for the identification of compounds that either specifically interact with these cis-acting elements or that act upstream of the signal transduction pathway that leads to activation of genes the cis-acting elements were derived from.

Thus, the present invention further relates to a method for the identification of an activator or inhibitor of genes specifically expressed in plants upon pathogen infection comprising the steps of:

(a) providing a plant, plant cell, or plant tissue comprising a recombinant DNA molecule comprising a readout system operatively linked to the chimeric promoter of the invention;

(b) culturing said plant cell or tissue or maintaining said plant in the presence of a compound or a sample comprising a plurality of compounds under conditions which permit expression of said readout system;

(c) identifying or verifying a sample and compound, respectively, which leads to suppression or activation and/or enhancement of expression of said readout system in said plant, plant cell, or plant tissue.

For the identification of inhibitors, it is advantageous to include an elicitor or another activator known to be capable of inducing the activity of promoters that contain the cis-acting elements of the chimeric promoters of the invention in step (b) of the above-described method, and to determine whether the compound to be screened suppresses the induction of the readout system by said elicitor or activator.

The term "readout system" in context with the present invention means a DNA sequence which upon transcription and/or expression in a cell, tissue or organism provides for a scorable and/or selectable phenotype. Such readout systems are well known to those skilled in the art and comprise, for example, recombinant genes and marker genes as described above and in the appended examples.

The term "plurality of compounds" in a method of the invention is to be understood as a plurality of substances which may or may not be identical.

Said compound or plurality of compounds may be comprised in, for example, samples of inorganic or organic molecules or, e.g., cell extracts from, e.g., plants, animals or microorganisms. Furthermore, said compound(s) may be known in the art but hitherto not known to be capable of suppressing or activating pathogen related genes. Suitable set ups for the method of the invention are known to the person skilled in the art. The plurality of compounds may be, e.g., added to the cell or tissue culture medium or soil, injected into the cell or sprayed onto the plant.

If a sample containing a compound or a plurality of compounds is identified in the method of the invention, then it is either possible to isolate the compound from the original sample identified as containing the compound capable of suppressing or activating the chimeric promoter of the invention, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. Preferably, the compound identified according to the above described method or its analog or derivative is further formulated in a form suitable for the application in plant breeding or plant cell and tissue culture. For example, it can be combined with a agriculturally acceptable carrier known in the art.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1(1995), 879-880; Hupp, Cell 83(1995), 237-245; Gibbs, Cell 79(1994), 193-198 and references cited supra). Furthermore, genes encoding a putative regulator of genes controlled by the cis-acting elements of the invention and/or which exert their effects up- or downstream from such genes may be identified using, for example, insertion mutagenesis using, for example, gene targeting vectors known in the art (see, e.g., Hayashi, Science 258(1992), 1350-1353; Fritze and Walden, Gene activation by T-DNA tagging. In Methods in Molecular biology 44(Gartland, K. M. A. and Davey, M. R., eds). Totowa: Human Press (1995), 281-294) or transposon tagging (Chandlee, Physiologia Plantarum 78 (1990), 105-115).

Said compounds can also be functional derivatives or analogues of known inhibitors or activators. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art or as described in the appended examples. Furthermore, peptidomimetics and/or computer aided design of appropriate derivatives and analogues can be used. The cell or tissue that may be employed in the method of the invention preferably is a plant cell, plant tissue or plant of the invention described in the embodiments hereinbefore.

In an additional embodiment, the characteristics of a given compound may be compared to that of a cell contacted with a compound which is either known to be capable or incapable of suppressing or activating the chimeric promoter of the invention or the promoter the cis-acting element of the chimeric promoter is derived from.

The inhibitor or activator identified by the above-described method may prove useful as a plant protective agent or herbicide or pesticide. Thus, in a further embodiment the invention relates to a compound obtained or identified according to the method of the invention said compound being an activator or an inhibitor of genes specifically induced upon pathogen infection.

Furthermore, identification of trans-acting factors which interact with the cis-acting elements of the invention can form the basis for the development of novel agents for modulating conditions associated with plant diseases. Identification of trans-acting factors is carried out using standard methods in the art (see, e.g., Sambrook, supra, and Ausubel, supra). To determine whether a protein binds to the cis-acting elements of the invention standard DNA footprinting and/or native gel-shift analyses can be carried out. In order to identify the trans-acting factor which binds to the cis-acting elements of the invention, these elements can be used as an affinity reagent in standard protein purification methods, or as a probe for screening an expression library. Once the trans-acting factor is identified, modulation of its binding to the cis-acting elements of the invention can be pursued, beginning with, for example, screening for inhibitors of trans-acting factor binding.

Activation or repression of genes involved in plant defense reactions could then be achieved in plants by applying of the trans-acting factor (or its inhibitor) or the gene encoding it, e.g. in a vector for transgenic plants. In addition, if the active form of the trans-acting factor is a dimer, dominant-negative mutants of the trans-acting factor could be made in order to inhibit its activity. Furthermore, upon identification of the trans-acting factor, further components in the pathway leading to activation (e.g. signal transduction) or repression of pathogenesis related genes then can be identified. Modulation of the activities of these components can then be pursued, in order to develop additional agents and methods for modulating the response of plants upon pathogen attack in plants.

Accordingly, the present invention also relates to a plant protection composition comprising the compound identified and obtained by the above described methods. The plant protection composition can be prepared by employing the above-described method of the invention and synthesizing the compound identified as inhibitor or activator in an amount sufficient for use in agriculture. Thus, the present invention also relates to a method for the preparation of an agricultural plant protection composition comprising the above-described steps of the method of the invention and synthesizing the compound so identified or an analog or derivative thereof.

In the plant protection composition of the invention, the compound identified by the above-described method may be preferentially formulated by conventional means commonly used for the application of, for example, herbicides and pesticides or agents capable of inducing systemic acquired resistance (SAR). For example, certain additives known to those skilled in the art stabilizers or substances which facilitate the uptake by the plant cell, plant tissue or plant may be used, for example, harpins, elicitins, salicylic acid (SA), benzol(1,2,3) thiadiazole-7-carbothioic acid (BTH), 2,6-dichloro isonicotinic acid (INA), jasmonic acid (JA), methyljasmonate.

In a further embodiment, the present invention relates to an antibody specifically recognizing the compound obtainable by the method of the invention or the cis-acting element described above. The antibodies of the invention can be used to identify and isolate other activators and inhibitors of genes that are involved in plant defense. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988.

Furthermore, the present invention relates to a diagnostic composition comprising the chimeric promoter, the recombinant gene, the vector, the compound or the antibody of the invention, and optionally suitable means for detection. Said diagnostic compositions may be used for, e.g., methods for screening activators or inhibitors as described above.

In addition, the present invention relates to a kit comprising the chimeric promoter, the recombinant gene, the vector, the compound or the antibody of the invention. The kit of the invention may contain further ingredients such as selection markers and components for selective media suitable for the generation of transgenic plant cells, plant tissue or plants. Furthermore, the kit may include buffers and substrates for reporter genes that may be present in the recombinant gene or vector of the invention. In addition, the kit of the invention may contain compounds such as elicitors, preferably fungal elicitors that can be used as standards for the expression assays. The kit of the invention may advantageously be used for carrying out the method of the invention and could be, inter alia, employed in a variety of applications referred to herein, e.g., in the diagnostic field or as research tool. The parts of the kit of the invention can be packaged individually in vials or in combination in containers or multicontainer units. Manufacture of the kit follows preferably standard procedures which are known to the person skilled in the art.

The kit or its ingredients according to the invention can be used in plant cell and plant tissue cultures, for example, for any of the above described methods for detecting inhibitors and activators of pathogenesis related genes. The kit of the invention and its ingredients are expected to be very useful in breeding new varieties of, for example, plants which display improved properties such as disease resistance.

It is also immediately evident to the person skilled in the art that the chimeric promoters, recombinant genes and vectors of the present invention can be employed to produce transgenic plants with a desired trait (see for review TIPTEC Plant Product & Crop Biotechnology 13(1995), 312-397) comprising (i) insect resistance (Vaek, Plant Cell 5(1987), 159-169), (ii) virus resistance (Powell, Science 232 (1986), 738-743; Pappu, World Journal of Microbiology & Biotechnology 11(1995), 426-437; Lawson, Phytopathology 86(1996), 56 suppl.), (iii) resistance to bacteria, insects and fungi (Duering, Molecular Breeding 2 (1996), 297-305; Strittmatter, Bio/Technology 13(1995), 1085-1089; Estruch, Nature Biotechnology 15 (1997), 137-141), (iv) inducing and maintaining male and/or female sterility (EP-A1 0 412 006; EP-A1 0 223 399; WO93/25695) or may be used as highly inducible production systems of heterologous proteins or biopolymers in plants analogous to inducible systems in bacteria.

The present invention for the first time demonstrates that a number of cis-acting elements that are responsible for inducibility of pathogenesis-related genes can be used either alone or in combination with themselves or with other cis-acting elements to construct chimeric promoters that are capable of mediating highly inducible gene expression in plant cells upon elicitor treatment. It is therefore evident that cis-acting elements derived, e.g., from pathogen-related promoters other than those specifically described above can be used in accordance with the present invention, for example, chitinase promoters; see, e.g., Kellmann, Plant. Mol. Biol. 30(1996), 351-358. Appropriate promoters that provide a source for such cis-acting elements can be used and obtained from any plant species, for example, maize, potato, sorghum, millet, coix, barley, wheat and rice. Such promoters are characterized by their inducibility upon pathogen infection.

For example, using cDNA of proteins that are specifically expressed in plants upon pathogen attack as probes, a genomic library consisting of plant genomic DNA cloned into phage or bacterial vectors can be screened by a person skilled in the art. Such a library consists, e.g., of genomic DNA prepared from plant leaf tissue, fractionized in fragments ranging from 5 kb to 50 kb, cloned into the lambda vectors such as Lambda EMBL3 or 4, Lambda ZAP, Lambda DASH or Lambda GEM. Phages hybridizing with the probes can be purified. From the purified phages DNA can be extracted and sequenced. Having isolated the genomic sequences corresponding to the genes encoding the PR proteins, it is possible to fuse heterologous DNA sequences to these promoters or their regulatory sequences via transcriptional or translational fusions according to methods well known to the person skilled in the art. In order to identify the regulatory sequences and specific elements of the these genes, 5'-upstream genomic fragments can be cloned in front of marker genes such as luc, gfp or the GUS coding region and the resulting chimeric genes can be introduced by means of *Agrobacterium tumefaciens* mediated gene transfer into plants or transfected into plant cells or plant tissue for transient expression. The expression pattern observed in the transgenic plants or transfected plant cells containing the marker gene under the control of the isolated regulatory sequences reveal the boundaries of the promoter and its cis-acting elements. The isolation of cis-acting elements having the above defined properties can be done by conventional techniques known in the art, for example, by using DNAseI footprinting and loss- and gain-of-function experiments. It is then possible to isolate the corresponding promoter region by conventional techniques and test it for its expression pattern. For this purpose, it is, for instance, possible to fuse the putative cis-acting element with a minimal promoter to a reporter gene, such as GUS, luciferase or green fluorescent protein (GFP) and assess the expression of the reporter gene in transient expression assays or transgenic plants; see also the appended examples.

Thus, the present invention relates to the use of a cis-acting element sufficient to direct elicitor-specific expression and in particular to the use of the chimeric promoter, the recombinant gene, the vector, the cis-acting element and/or the compound of the present invention for the production of pathogen resistant plants or for identifying and/or producing compounds capable of conferring induced resistance to a pathogen in a plant.

In a still further embodiment, the present invention relates to a method of rendering a gene responsive to pathogens comprising inserting at least one cis-acting element sufficient to direct elicitor-specific expression into the promoter of said gene. As is evident to the person skilled in the art a promoter that displays the capabilities of the chimeric promoter of the invention can also be obtained by introducing the cis-acting element as defined above into a promoter of a gene, preferably in close proximity to the transcription initiation site of the gene.

In another embodiment, the present invention relates to a method for preparing a promoter capable of mediating local gene expression in plants upon pathogen infection comprising operably linking a cis-acting element sufficient to direct elicitor-specific expression to a transcription initiation sequence of a promoter. Preferably, said cis-acting element to be inserted in the above-described methods is a cis-acting element of the present invention or as defined in the foregoing embodiments or a multimeric form thereof as defined hereinabove. As mentioned before, the elicitor responsive cis-acting elements are preferably responsive to fungal elicitor.

In a preferred embodiment of the invention, the above-described methods further comprising deleting non-specific cis-acting elements in the promoter. Introduction of the cis-acting element of the invention into a given promoter per se may not be sufficient to direct the promoter to exclusively mediate local gene expression in plants upon pathogen infection. In this case, preexisting elements that may be responsive, for example, to light, hormones, low temperatures, drought or salt stress may be deleted.

The above described methods give rise to novel chimeric promoters that are at least partially, preferably fully controlled by plant/pathogen interaction.

Accordingly, the present invention also relates to the promoter obtainable by a method as described above. Said promoter can then be employed for the embodiments described hereinabove.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet. Further databases and public website addresses are known to the person skilled in the art and can also be obtained using known websites for Internet search engines. An overview of patent information in biotechnology and a survey of relevant sources of patent information useful for retrospective searching and for current awareness is given in Berks, TIBTECH 12(1994), 352-364.

The present invention is further described by reference to the following non-limiting examples.

The Examples illustrate the invention:

Experimental Setup

1. Recombinant DNA Techniques

Unless stated otherwise in the examples, all recombinant DNA techniques are performed according to protocols as described in Sambrook (1989), Molecular Cloning: A Laboratory Manual. Cold Spring Harbor Laboratory Press, NY or in Volumes 1 and 2 of Ausubel (1994), Current Protocols in Molecular Biology, Current Protocols. Standard materials and methods for plant molecular work are described in Plant Molecular Biology Labfase (1993) by R. D. D. Croy, jointly published by BIOS Scientific Publications Ltd. (UK) and Blackwell Scientific Publications (UK).

2. Transient Expression Vector

Figure 2:
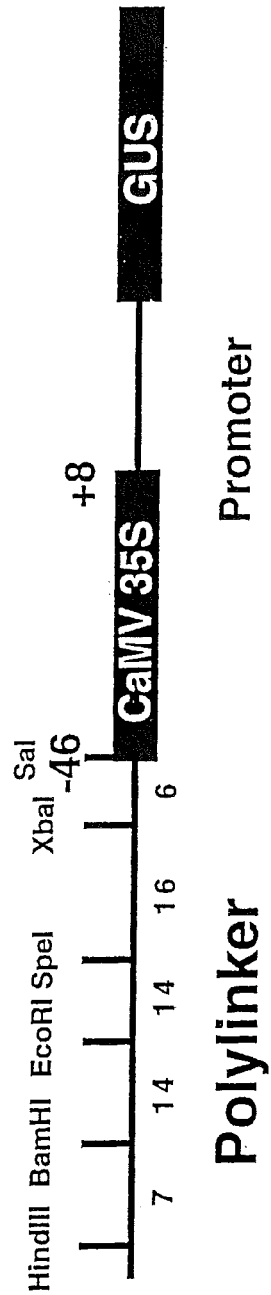
FIG. 2 shows an overview cartoon of the plasmid ms23. The Gus reporter gene and minimal −46 CaMV 35S promoter are shown, as are restriction sites found in the polylinker sequence situated 5' to the minimal promoter. The distances (in base pairs) between the restriction sites are also shown.

All constructs, unless a different protocol is given in the examples, were cloned between the SpeI and XbaI sites in pbt10-GUS (ms23) (Sprenger, 1997). At the 3' end of each construct is an intact XbaI site (6 bp) followed immediately by a minimal CaMV 35S promoter (−46 to +8). The 3' end of all inserts are therefore 28 bp upstream of the CaMV TATA Box and 52 bp upstream of the start of transcription. Multiple copies of the elements are separated by 6 base pairs (TCTAGT) created by the ligation of a SpeI sticky end with a XbaI sticky end. The sequence of ms23(SEQ ID NO: 17) as a restriction map and an overview cartoon are provided (FIGS. 1 and 2).

3. Transgenic Plant Vector

Figure 3:
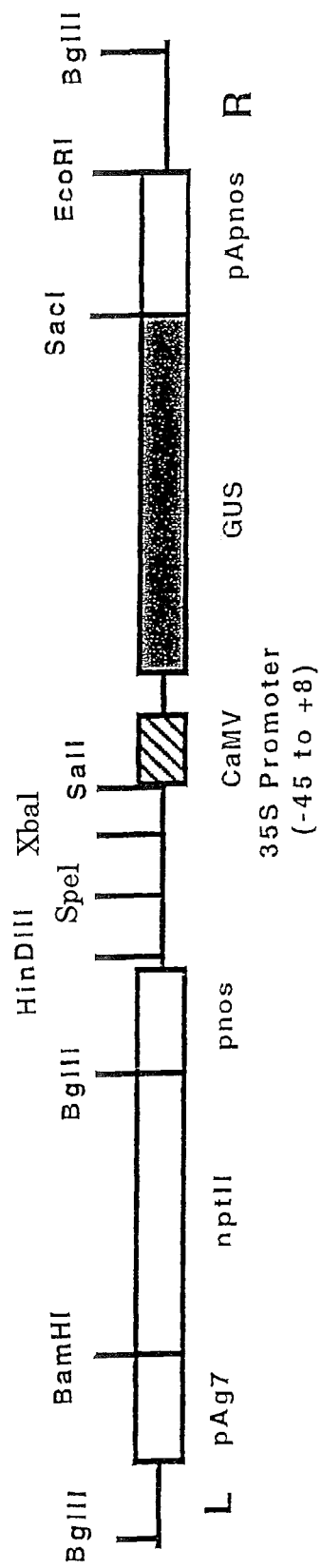
FIG. 3 shows an overview cartoon of the plasmid pGPTV. The Gus reporter gene and minimal −46 CaMV 35S promoter are shown as are the SpeI and XbaI sites used in making the constructs employed. The nptII selection marker is also indicated, as are the left and right T-DNA borders (L and R). The terminators (pApnos and pnos) and promoter driving the nptII gene (pAg7) are also shown.

The vector employed was pGPTV-GUS-kan (Becker, Plant Mol. Biol. 20 (1992), 1195-1197). The polylinker, minimal CaMV 35S promoter and GUS reporter gene are identical to ms23. All spacings and orders of cis-elements within the constructs are therefore identical to those in the corresponding transient expression constructs in ms23. A cartoon of pGPTV is provided (FIG. 3).

4. Transient Transfection and Expression Assays

The transient transfection and expression assays were essentially carried out as described in Dangl, EMBO J. 6(1987), 2551-2556; Schulze-Lefert, EMBO J. 8(1989), 651-656; van de Löcht, EMBO J. 9(1990), 2945-2950. Briefly, five day old subcultured parsley cells are used for the isolation of protoplasts. Protoplasting is achieved by overnight incubation of the cells in 0.24 M $CaCl_2$ containing 0.25% (w/v) cellulase and 0.05% (w/v) macerozyme at 24° C. Protoplasts are collected by centrifugation (7 min., 100 g), washed with 0.24 M $CaCl_2$, and then floated in B5 medium (GIBCO/BRL) containing 0.4 M sucrose and 1 mg/ml 2,4-dichlorophenoxyacetic acid. Protoplasts floating after centrifugation (5 min, 100 g) were harvested, counted and adjusted to $2 \times 10^6$/ml.

Supercoiled or linearized plasmid DNA (5-20 µg) containing the chimeric promoter-reporter (GUS) construct was transferred into the protoplasts using the polyethylene glycol (PEG) method (Krens, Nature 296(1982), 72-74). Each transformation assay was split and placed into two 3 ml plates. The Pep25(Nürnberger, Cell 78(1994), 449-460) elicitor was added to one whereas the other served as a control. Both samples were harvested after 8 hours, frozen in liquid nitrogen, crude protein extracts prepared and GUS activity assayed (Jefferson, Plant Mol. Biol. Rep. 5 (1987), 387-405). Bradford assays (Bio-Rad) were used for protein determination. The expression data are given as mean fold induction values±standard deviation (SD) and mean GUS activity (pmol/min/mg) from six independent transient transfection assays treated with or without Pep25 elicitors.

5. Generation of Transgenic Plants

Transgenic plants were generated according to the methods described in Bechtold, Mol. Biol. Genet. 316(1993), 1194-1199; Grant, Science 269(1995), 843-846 and Dangl, Science 269 (1995), 843-846. Briefly, the promoter elements were cloned in front of the reporter gene of the binary vector pGPTV-GUS-kan (Becker, Plant Mol. Biol. 20(1992), 1195-1197) and the constructs introduced into the *Agrobacterium* strain GV3101 (pMP90; (Koncz and Schell, loc. cit.) containing the pMP90 helper plasmid. 500 ml cultures were grown in YEB medium containing kanamycin (50 µg/ml), rifampicin (100 µg/ml) and gentamycin (25 µg/ml). Cells were resuspended in infiltration medium (0.5× Murashige-Skoog salts; 1×B5 vitamins; 5.0% sucrose and 0.044 µM benzylaminopurine) and vacuum infiltrated into *Arabidopsis* plants by the method of Grant (1995). T1 seeds were surface-sterilized and transformants were selected on MS medium containing 50 µg/ml kanamycin. Primary transformants were transferred to soil and tested for GUS expression during pathogenesis and biotic or abiotic stress.

EXAMPLE 1

Box S is Capable of Mediating Elicitor Induced Gene Expression

Box S (CAGCCACCAAAGAGGACCCAGAAT; SEQ ID NO: 7) has been shown to be necessary for the elicitor-responsive expression of the parsley eli 7 genes (Takamiya-Wik, Ph.D. thesis, University of Köln, Köln, Germany (1995)). Together with the results concerning Box N (see Example 4.3) for the first time the core sequence of this type of element has been defined which appears to be AGCCAC-CANA (SEQ ID NO: 14). The element is not identical to any known elicitor-responsive element although it is very similar to a number of ethylene response elements that have the core sequence AGCCGCC (GCC Boxes) (Ohme-Takagi and Shinshi, The Plant Cell 7(1995), 173-182). In the promoters investigated (eli7-1, eli7-2 and Prp1) there is always an A residue rather than a G. What difference this difference in sequence makes is at present unclear and it is not known whether Box S is responsive to ethylene. It has however been shown for the first time that the Box S elements with the sequence AGC-CACC are elicitor-responsive elements. The present data also show for the first time that GCC Boxes are also elicitor response elements as well as being ethylene response elements. Box S is a very strong elicitor-responsive element. A monomer of Box S gives 11-fold inducibility and a tetramer up to 560-fold inducibility. This clearly shows Box S to be an extremely promising element for biotechnological purposes.

The sequence of the monomer element used is: 5'-actagt-CAGCCACCAAAGAGGACCCAGAATtctaga-3' (SEQ ID NO: 19) with the element in upper case letters and the SpeI/XbaI ends in lower case letters. Constructs containing 1, 2, 4 and 8 copies of Box S were constructed and subjected to a transient expression assay as described above. The results were as follows:

|  | Minus elicitor | Plus elicitor | Fold induction |
| --- | --- | --- | --- |
| 1 × S | 168 | 2058 | 12 |
| 2 × S | 118 | 10781 | 91 |
| 4 × S | 187 | 76904 | 441 |
| 8 × S | 781 | 102211 | 130 |

These Box S constructs are novel and have high inducibility. Four copies of Box S appears to be the best with a very low background value (187) a high induced level (76904) and a very high fold induction (441×, the highest of any of the constructs tested).

EXAMPLE 2

Box D is Capable of Mediating Elicitor Inducible Gene Expression

Box D (TACAATTCAAACATTGTTCAAACAAG-GAACC; SEQ ID NO: 11) is present in the parsley PR2 promoter and has never before been reported to be a cis-acting element. Box D was identified by DNaseI footprinting, by loss of function experiments in the context of the PR2 promoter and by gain-of-function experiments with monomers and multimers. Box D is a very strong elicitor-responsive element, a tetramer directing 10-fold elicitor-inducibility combined with a very high level of expression, whilst a dimer is less strong but gives 15-20-fold inducibility. This clearly shows Box D to be a promising element for biotechnological purposes.

The sequence of the element used is: 5'-actagtTACAAT-TCAAACATTGTTCAAACAAGGAACCtctaga-3' (SEQ ID NO: 20) with the element in upper case letters and the SpeI/XbaI ends in lower case letters. Constructs containing 1, 2 and 4 copies of Box D were constructed and subjected to the transient expression assay described above. The results were shown below.

|  | Minus elicitor | Plus elicitor | Fold induction |
| --- | --- | --- | --- |
| 1 × D | 346 | 4002 | 11 |
| 2 × D | 1562 | 31331 | 20 |
| 4 × D | 5519 | 61552 | 11 |

These Box D constructs are novel. Two copies of Box D may be the best with a moderate background value (1562), a high induced level (31331) and a good fold induction (20×).

EXAMPLE 3

Box U Provides for Elicitor Inducible Gene Expression

Box U (ATGAAGTTGAAATTCAATAG; SEQ ID NO: 13) is present in the parsley PR2 promoter and has never before been reported to be a cis-acting element. Box U has been defined by DNaseI footprinting, by loss of function experiments in the context of the PR2 promoter and by gain-of-function experiments with monomers and multimers. Box U is a reasonably strong elicitor-responsive element, a tetramer directing 40-fold elicitor-inducibility.

The sequence of the element used is: 5'-actagtAGT-TGAAATTCAATAA-GTTGAAATTCAATAtctaga-3' (SEQ ID NO: 21) with the element in upper case letters and the SpeI/XbaI ends in lower case letters.

Constructs containing 2 copies of the above Box U sequence were constructed. The results of a transient expression assay are shown below. These therefore contain 4 copies of the Box U element (AGTTGAAATTCAATA; SEQ ID NO: 12). 1 or 2 copies of Box U are also active.

|  | Minus elicitor | Plus elicitor | Fold induction |
| --- | --- | --- | --- |
| 4 × U | 100 | 3947 | 39 |

These Box U constructs are novel. Box U appears to be a moderately strong pathogen-responsive element with a good fold induction (about 40×).

EXAMPLE 4

Some W Boxes are Capable of Mediating Elicitor Inducible Gene Expression

The results obtained in accordance with the present invention clearly show that there are great differences between the different W Boxes that have been tested. Some are very strong (Box W2), some weak (Box W1), some are not active at all on their own (Box W3) and some are present as composite elements together with other cis-acting elements (Box N). The W Boxes also have differences outside of the core TGAC sequences:

Box W1: TTTGACC (SEQ ID NO: 1)

Box W2: TTCAGCC-$N_7$-TTGACC (SEQ ID NO: 3)

Box W3: TGAC-$N_6$-GTCA (SEQ ID NO: 5)

Box N: TTTGACC plus GCCACC (S Box) (SEQ ID NO: 8)

Box $W_{Amy}$: TTGACC within TGAC-$N_6$-GTCA palindrome (SEQ ID NO: 6)

4.1 Box W1

Box W1(CACACTTAATTTGACCGAGTAACAT-TCGCC; SEQ ID NO: 2) has previously been identified as a weak elicitor-responsive cis-element in the parsley PR1 promoters and a tetramer has been shown to be sufficient to direct elicitor-responsive expression in the parsley transient expression system (Rushton, 1996). Box W1 contains the W box sequence TTGACC and evidence suggests that these elements are bound by the WRKY class of transcription factors. As W boxes have also been found in the monocots Wild oat (Rushton, 1995) and maize (Raventos, 1995) and WRKY proteins have been found in an increasing number of plant species this suggests that the W box elements may be cis-acting elements in all plant species. Box W1 had never before been tested on its own for activity as a monomer or in combination with other elements and it was observed that a monomer directs elicitor-inducible expression (5-fold inducibility) and that Box W1 is also active in combination with other elements (see below).

The current results show Box W1 itself, however, to be a weak element. The sequence of the element used (the monomer) is: 5'-actagtCACACTTA-ATTTGACCGAGTAACAT-TCGCCtctaga-3' (SEQ ID NO: 22) with the element in upper case letters and the SpeI/XbaI ends in lower case letters. This construct is slightly different than the construct previously reported (Rushton, 1996) as the element is inserted into the SpeI/XbaI sites and not BamHI/BglII. Constructs containing 1, 2 and 4 copies of Box W1 were constructed and subjected to the transient expression assay. The results were as follows.

|  | Minus elicitor | Plus elicitor | Fold induction |
| --- | --- | --- | --- |
| 1 × W1 | 362 | 1495 | 4.1 |
| 2 × W1 | 299 | 2433 | 8.1 |
| 4 × W1 | 56 | 870 | <15 |

The fold induction with 4×W1 is similar to the previously reported values (Rushton, 1996). Comparison with values for other elements shows Box W1 to be a weak element.

4.2 Box W2

Box W2(TTATTCAGCCATCAAAGTTGACCAATAAT; SEQ ID NO: 4) has previously been identified as a cis-acting element required for the elicitor responsive expression of parsley PR1 promoters in the transient expression system (Rushton, 1996). However, gain of function has been first demonstrated in accordance with the present invention. Box W2, like Box W1, contains a TTGACC element but the rest of the element is totally different and these other sequences play an important role, as a tetramer of Box W1 is a weak element with about 10-fold elicitor inducibility whereas Box W2 directs levels of expression up to 100 times higher than Box W1 with a 50-fold elicitor inducibility. It is shown for the first time that Box W2 alone, as a monomer or multimer, is a very strong elicitor-responsive element and that it is also active in combination with other elements.

The sequence of the element used (the monomer) is: 5'-actagtTTATTCAGCCATCAAAGTTGACCAATAATtctaga-3' (SEQ ID NO: 23) with the element in upper case letters and the SpeI/XbaI ends in lower case letters. Constructs containing 1, 2, 4 and 8 copies of Box W2 were constructed and subjected to the transient expression assay. The following results were obtained.

|  | Minus elicitor | Plus elicitor | Fold induction |
| --- | --- | --- | --- |
| 1 × W2 | 770 | 8914 | 11 |
| 2 × W2 | 998 | 46651 | 46 |
| 4 × W2 | 2375 | 105685 | 44 |
| 8 × W2 | 7680 | 164454 | 21 |

W2 is the strongest elicitor-responsive cis-acting element that has been so far tested, eight copies of W2 giving GUS values of approximately 164,000.

4.3 Box N

Box N comes from the potato gst1 gene (TTCTAGCCAC-CAGATTTGACCAAAC; SEQ ID NO: 9) and has never previously been defined. It contains both an S Box sequence (AGCCACCAGA) (SEQ ID NO: 24) and a W Box sequence (TTGACC) within just 25 base pairs and as such represents a novel cis-element composed of two types of elicitor response element within a very small stretch of DNA. A tetramer of Box N gives at least 75-fold elicitor inducibility. This observation suggests three important conclusions; firstly that Box N may be extremely useful for biotechnological applications, secondly that the core Box S sequence is AGCCACCANA (SEQ ID NO: 14) and thirdly that Boxes S and W may represent a common theme in plant promoters that respond to pathogens as these elements are present in both parsley and potato. Box N alone is a strong elicitor-responsive element and extremely interesting, as it consists of an S Box (GCCACC) followed by a W Box (TTTGACC).

The sequence of the element used (the monomer) is: 5'-actagtTTCTAGCCACCAGATTTGACCAAACtctaga-3' (SEQ ID NO:18) with the element in upper case letters and the SpeI/XbaI ends in lower case letters. A construct with four copies of Box N was tested in transient expression assay. The results were as follows.

|  | Minus elicitor | Plus elicitor | Fold induction |
| --- | --- | --- | --- |
| 4 × N | 1085 | 92980 | 85 |

Box N is a strong element and shows a very high fold inducibility. This novel combination and spacing of W and S Box elements may prove to be very useful for biotechnological purposes.

4.4 Box $W_{Amy}$

Box $W_{Amy}$ comes from the wild oat α-Amy2/A and wheat α-Amy2/54 genes where it has previously been published under the name Box 2 or O2S (see Rushton, Plant Mol. Biol. 29 (1995), 691-702). It is a cis-acting element required for the transcriptional activation of these genes during germination but has never previously been linked to a role in pathogenesis. Box $W_{Amy}$ consists of two W Box elements: a hexamer 5'-TTGACC-3' embedded in a palindromic 5'-TGAC-$N_6$-

GTCA-3'. As it contains both types of sequences together it constitutes a new type of W Box and may be a "super W Box."

The sequence of the element used (the monomer) is: 5'-actagtGGATTGACTTGACCGTCATCGGCTtctaga-3' (SEQ ID NO: 25) with the element in upper case letters and the SpeI/XbaI ends in lower case letters. A construct containing 7 copies of Box $W_{Amy}$ was constructed and to the transient expression assay. The result is shown below.

|  | Minus elicitor | Plus elicitor | Fold induction |
|---|---|---|---|
| 7 × $W_{Amy}$ | 168 | 43867 | 260 |

$W_{Amy}$ is a strong elicitor-responsive cis-acting element and has the highest fold induction of any W Box that has been so far tested. This element could therefore be a particularly effective W Box and could aid the designing of synthetic W Boxes that are even more effective.

EXAMPLE 5

Synthetic Promoters Consisting of Combinations of the Above-Described Elements

Synthetic promoters composed of combinations of the above elicitor-responsive elements have never before been constructed or tested. All elements (Boxes W1, W2, S, U, D, N and $W_{Amy}$) are active in combination with each other; monomer, dimer and tetramer constructs being active. The furthest downstream element (nearest to the TATA Box) has the strongest effect on the synthetic promoter with further upstream elements having a much lesser effect. However the combination of two or more different types of cis-element may have a much more profound effect on expression in planta. In addition the insertion of a spacer region composed of anything between 100 base pairs and 1,000 base pairs appears to increase the contribution of the more upstream cis-elements. All of these synthetic promoters are good candidate promoters that may be rapidly and locally responsive to pathogen attack but also show negligible activity in uninfected tissues. These promoters may therefore allow the engineering of defense reactions that are closely related to natural defense mechanisms without appreciable activity in non-infected cells of the plant.

A large number of combinations have been tested. The results for some of these are detailed below. All of these combinations are novel and these constructs represent true synthetic promoters. The elements are inserted into the SpeI/XbaI sites, as with all of the constructs, and read from the 5' end to the 3' end i.e. 4×W2/4×S is:

SpeI-W2-W2-W2-W2-S-S-S-S-XbaI

Generally, the elements nearest to the TATA Box (i.e. at the 3' end) have the greatest effect on both level of expression and fold induction. The effect of the upstream elements is often minimal and there is also an inhibitory effect probably due to steric hindrance when different elements are put close together; compare 4×S/4×W2 with (2×S/2×W2)×2. The insertion of spacer regions between elements is therefore recommended to alleviate problems due to steric hindrance. The results of the transient expression assays are shown below.

|  | Minus elicitor | Plus elicitor | Fold induction |
|---|---|---|---|
| 1 × S/1 × W2 | 1732 | 85126 | 49 |
| 2 × S/2 × W2 | 1529 | 95872 | 62 |
| 4 × S/4 × W2 | 2654 | 64105 | 24 |
| (2 × S/2 × W2) × 2 | 483 | 9832 | 20 |
| 4 × W2/4 × S | 2753 | 205826 | 74 |
| 1 × W2/1 × S | 146 | 2690 | 18 |
| 2 × S/2 × D | 191 | 15541 | 81 |
| 4 × S/4 × D | 9775 | 100265 | 10 |
| 1 × D/1 × S | 32 | 1246 | 38 |
| 4 × D/4 × S | 6795 | 204115 | 30 |
| 2 × W2/2 × D | 1762 | 32462 | 18 |
| 4 × W2/4 × D | 22042 | 92875 | 4.2 |
| 4 × D/4 × W2 | 18857 | 276456 | 14 |
| 1 × D/1 × W2 | 295 | 4369 | 14 |

Adding more copies of an element in a composite construct often increases the absolute level of expression (e.g. 2×W2/2×D and 4×W2/4×D) but often lowers the fold induction. In some cases even the absolute level of expression decreases (e.g. 2×S/2×W2 and 4×S/4×W2) and a comparison with (2×S/2×W2)×2 suggests that this is due to steric hindrance as the number of copies of the elements is the same, it is just the order that is changed.

EXAMPLE 6

Box E17 is Capable of Mediating Elicitor Induced Gene Expression

Box E17(TCAATATGTCAATGGTCAACATTCAAC; SEQ ID NO: 15) was isolated from the promoter of the parsley Eli17 gene which is known to react to elicitor-treatment with transcript accumulation (Somssich, Plant Mol. Biol. 12 (1989), 227-234). Recently it has been shown that the Eli17 gene reacts very rapidly and transiently to elicitor-treatment and pathogen infection. This has never been previously described.

Figure 4:
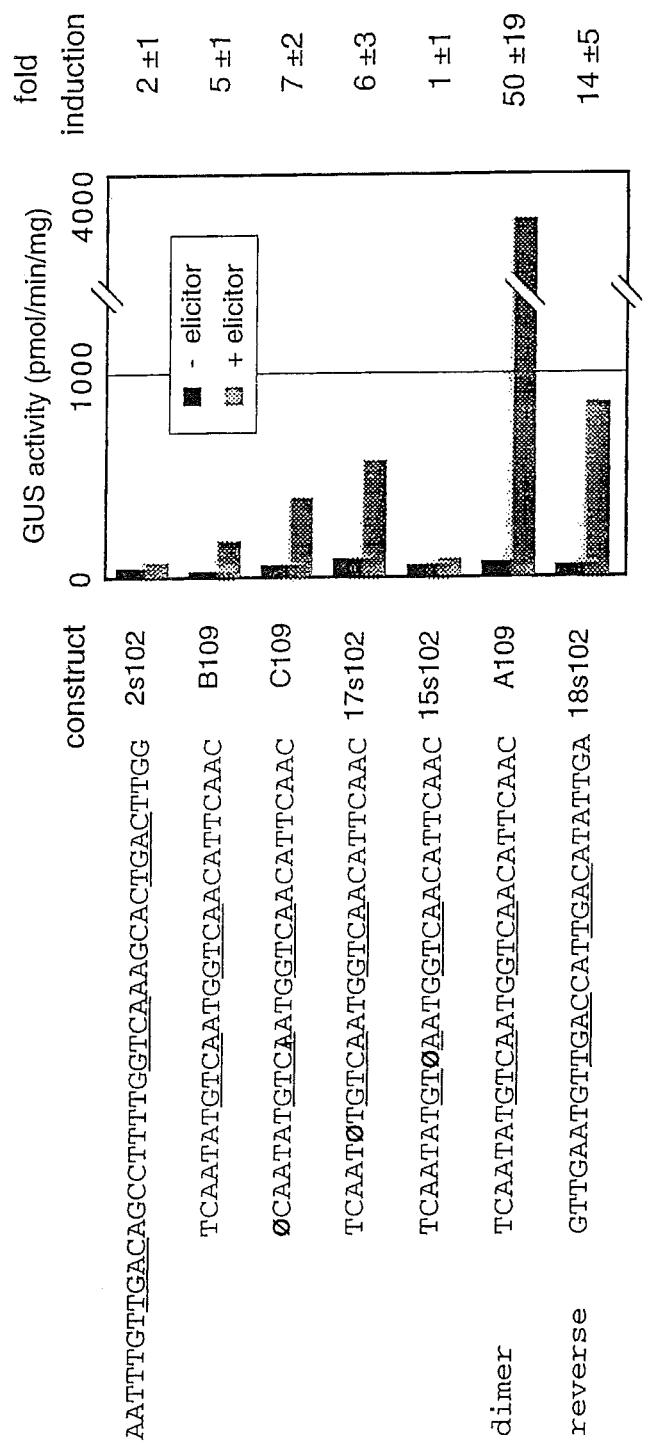
FIG. 4 shows elicitor inducibility of chimeric promoters containing Box E17 and derivatives thereof. GTAC motifs in forward and reverse orientation are underlined. Deleted bases are depicted as Ø. The depicted fragments are located 12 bp upstream of the 35S minimal promoter. The monomers of the dimeric construct A109 are separated by a 6 bp restriction site (SEQ ID NOS:27-31)

The sequence of the monomer element used is: 5'-actagt-TCAATA-TGTCAATGGTCAACATTCAACtctaga-3' (SEQ ID NO: 26) with the element in upper case letters and the SpeI/XbaI ends in lower case letters. Constructs containing 1 and 2 copies of Box E17 as well as a monomeric reverse complement of Box E17 were constructed (FIG. 4, constructs B109, A109, and 18S102, respectively) and subjected to a transient expression assay as described above. As shown in FIG. 4, the monomer has 5-fold inducibility and the dimer 50-fold. In comparison to the other cis-elements of the present invention moderate induction was achieved by Box E17. Likewise, a tetramer of Box E17 was subjected to transient assays (data not shown), which resulted in 5- to 20-fold induction following elicitor-treatment. However, this result cannot be compared to the induction values of the Box E17 constructs mentioned above because of diminished quality of the parsley protoplasts used. Presumably, the Box E17 tetramer mediates at least an induction as high-fold as the respective dimer.

Figure 5:
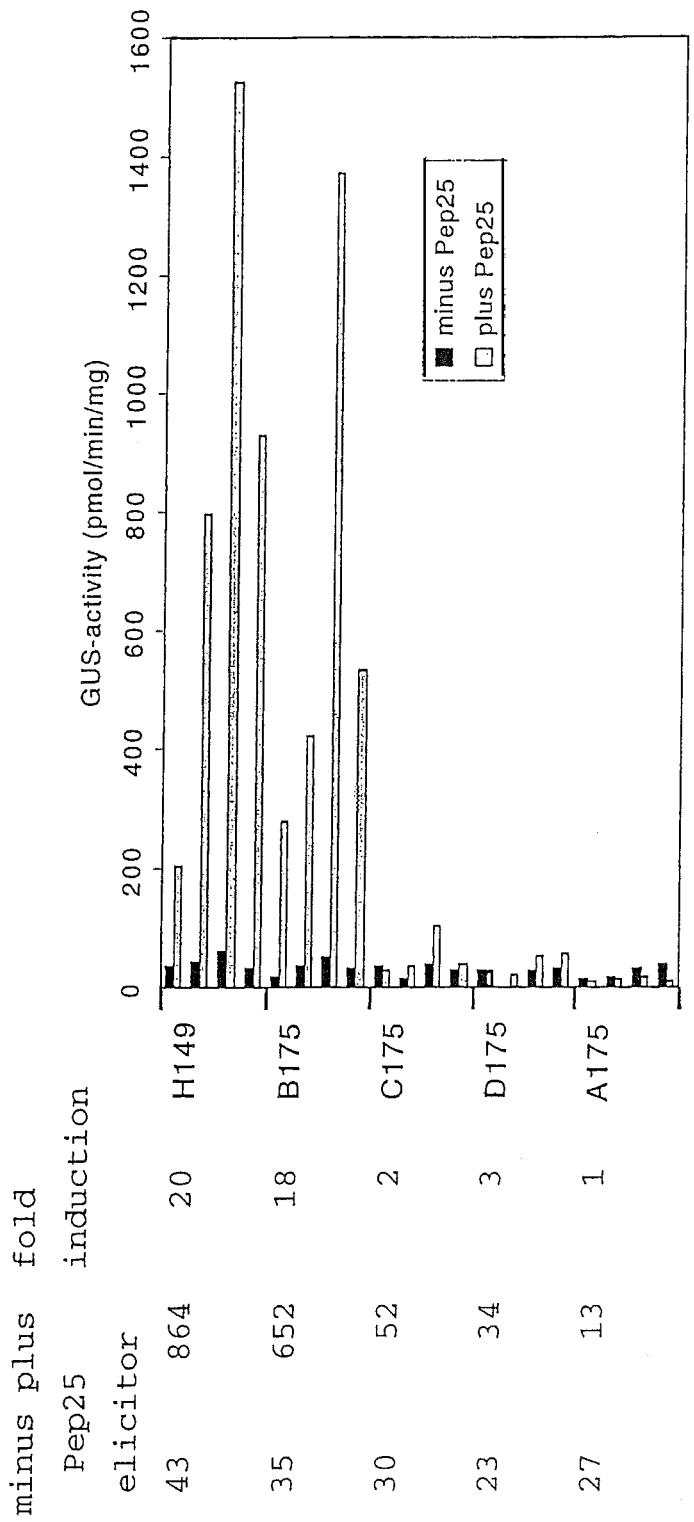
FIG. 5 shows elicitor inducibility of chimeric promoters containing dissected Box E17 elements. Starting from a Box E17 containing chimeric promoter (H149), chimeric promoters were constructed having 6 nucleotides deleted from the 5'-end of Box E17(B175), 7 nucleotides from its 3'-end (C175) or comprising both deletions (C175). Additionally, a promoter was tested comprising a 445 bp Eli17 promoter fragment from which the 27 bp Box Eli17 element was deleted (A175). Relative and absolute elicitor induction values are given that were measured in transient expression assays (SEQ ID NOS:32-35)

Similar to cis-elements of Example 4, Box E17 contains two copies of the W-Box core motif TGAC, in reverse orientation (GTCA) as tandem repeat separated by a 3 bp spacer. The importance of this core motif can be inferred from preliminary mutagenesis experiments (FIG. 4, constructs C109, 17S102, and 15S102). A 1 bp deletion within the W-Box motif resulted in complete loss of function in contrast to deletions at two different sites having no effect to inducibility. In order to further narrow down the minimal structure capable of mediating elicitor-responsiveness dissected Box E17 elements were tested in transient expression assays as described above. The initial Box E17(SEQ ID NO: 15) was deleted from the 5'-end by 6 bp, from the 3'-end by 7 bp and from both ends by 6 and 7 bp, respectively. Each of these oligonucleotides were ligated into the BamHI site of the MS23 vector, which was before cut with BamHI restriction enzyme and the overhangs blunted, giving rise to the promoter constructs H149, B175, C175 and D175 (FIG. 5). The promoter constructs showed remarkable differences regarding their elicitor-responsiveness. C175 and D175 having the 3'-end truncated, displayed no significant induction upon elicitor treatment. On the other hand, the 5'-truncated B 175 gave values which were similar to those of the 27 bp Box E17 element. Thus, also the 21 bp-element B175(SEQ ID NO: 16) is a functional cis-element in the sense of the present invention.

Furthermore, Box E17 is not only sufficient but also necessary to lend the Eli17 promoter, or at least a 445 bp long functional part thereof which comprises said element naturally, its elicitor inducibility. This could be shown in transient expression assays which were performed with an MS23-construct containing the 445 bp stretch having the 27 bp-element removed. The resulting complete loss of elicitor-dependent inducibility (see FIG. 5) indicates the crucial role of Box E17 for elicitor- and pathogenesis-related gene regulation in its natural environment and further supports its applicability for conferring inducibility upon elicitation or pathogenesis to a chimeric promoter according to the present invention.

EXAMPLE 7

Figure 6:
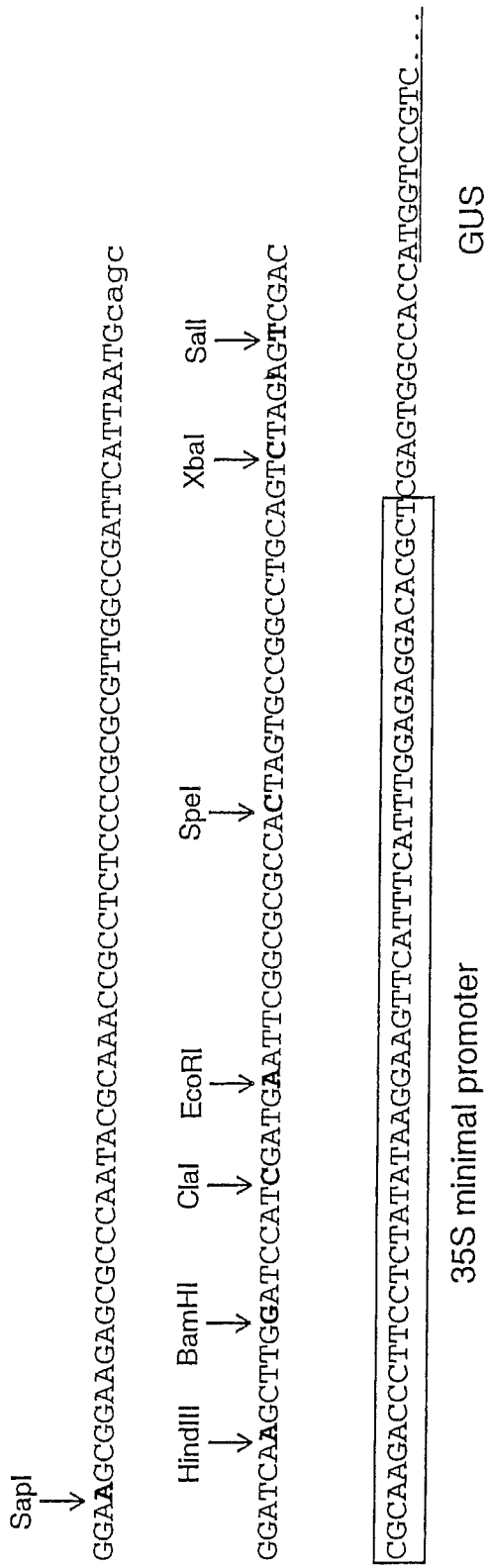
FIG. 6 shows a cut-out of the polylinker of the vector ms23. For measuring the influence of the distance to the 35S minimal promoter Box E17 or its dimer was inserted into eight different restriction sites (SEQ ID NO: 36)
Figure 7A:
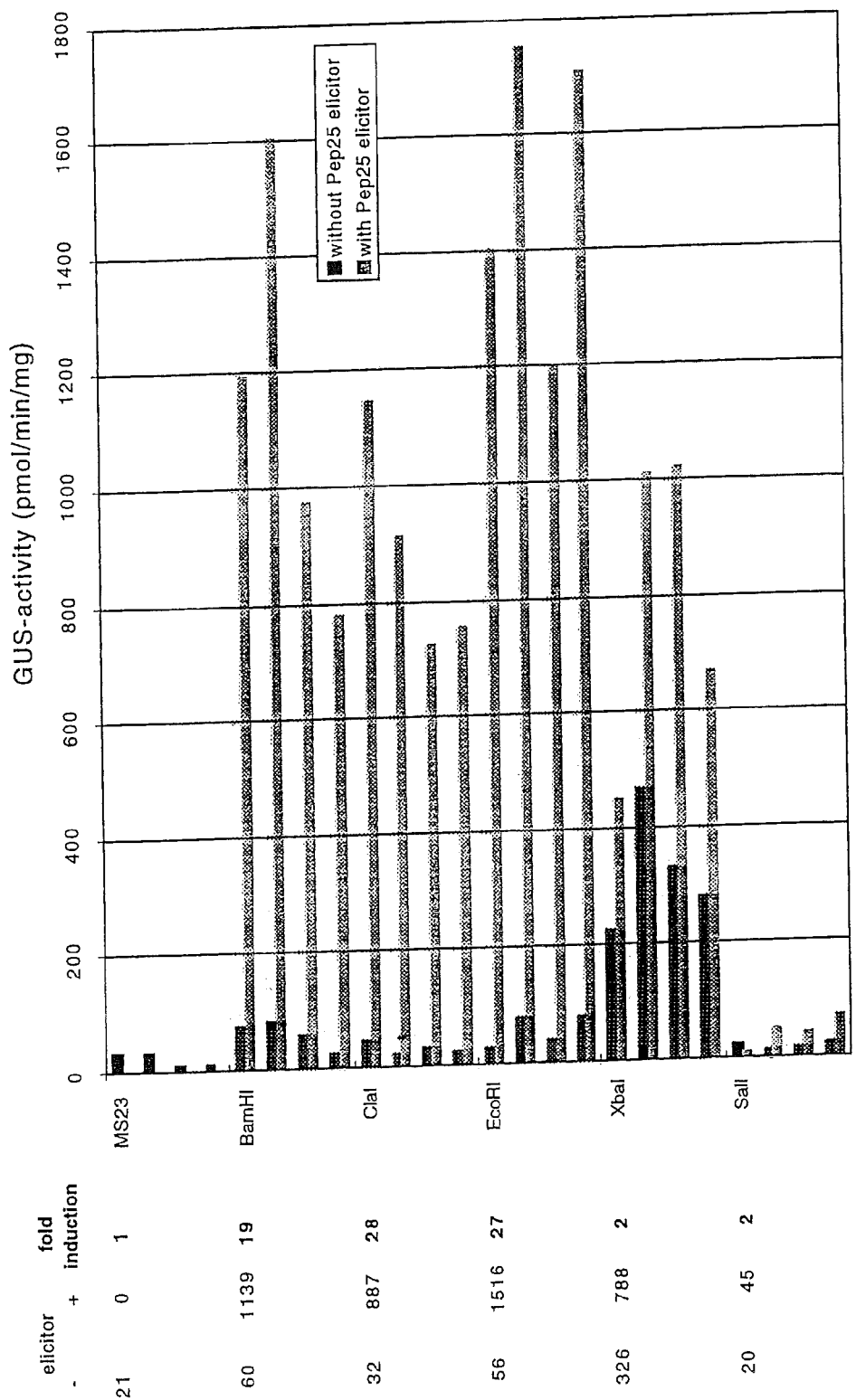
FIG. 7a shows the induction upon elicitor treatment for the BamHI, ClaI, EcoRI, XbaI, and SalI constructs.
Figure 7B:
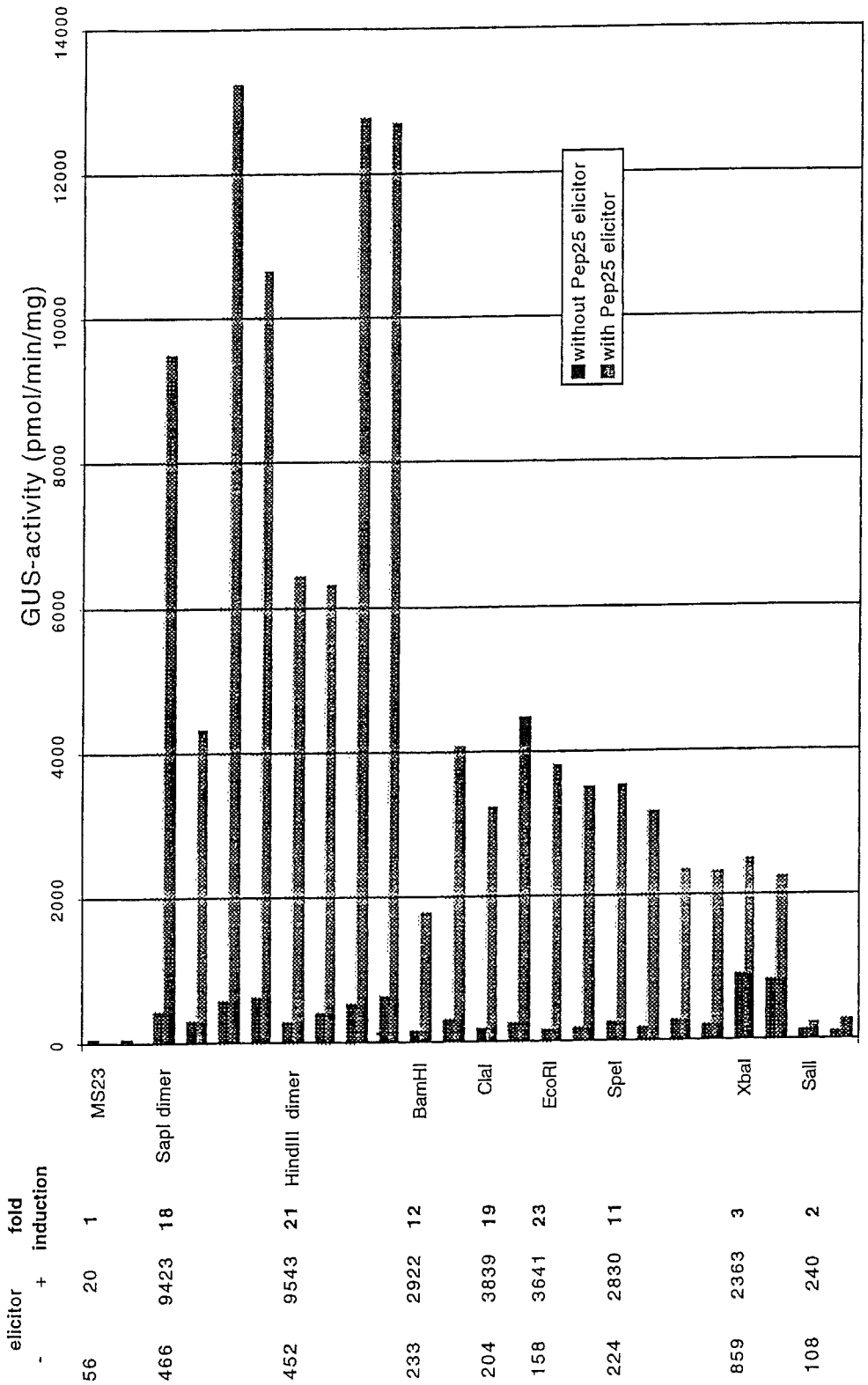
FIG. 7b shows, in another experiment, the induction for elicitor treatment for the SapI-dimer, HindIII-dimer, BamHI, ClaI, EcoRI, SpeI, XbaI, and SalI constructs. ms23, in FIGS. 7a and 7b, represents the vector only containing the minimal promoter as negative control.

Chimeric Promoters with Varying Distances of the Box E17 Element to the Minimal Promoter are Inducible In order to elucidate the optimal position of the Box E17 element within the chimeric promoter several constructs with varying distances to the 35S minimal promoter were tested (FIGS. 6 and 7). For this purpose Box E17 was inserted into different restriction sites of the ms23 polylinker. After digesting the vector and filling in the overhangs, the cis-element was blunt ligated into the respective site as a monomer or as a dimer. The transient assays were conducted as described above. The results (FIG. 7) indicate an optimal distance of Box E17 to the 5' end of the minimal promoter of 40 to 60 bp (corresponding to the restriction sites BamHI, ClaI, EcoRI). Still good induction was observed for the SapI site in 131 bp distance whereas considerably weaker response was obtained when Box E17 was inserted into the SalI site which is 5 bp upstream of the minimal promoter.

EXAMPLE 8

Transgenic Plants Carrying Chimeric Promoters

Transformants were tested for the response of the synthetic promoters to pathogens. Cultures of the bacterium pseudomonas (strains Rpt2 or Rpm1) were grown in King's-B Medium containing 30 µg/ml kanamycin and 100 µg/ml rifampicin. The bacteria were resuspended in 10 mM $MgCl_2$ at an $OD_{600}$ of 0.2 and infiltrated into leaves via a syringe. Controls were performed using 10 mM $MgCl_2$ alone. After 6 hours the leaves were removed from the plants and stained for GUS activity using X-Gluc. The expression pattern observed in the transgenic plants containing the GUS marker gene under the control of the chimeric promoter of the invention revealed expression in tissue infected by *Pseudomonas syringae* and in some cases also local expression in wounded tissues.

With regard to Box E17 a chimeric promoter comprising the dimer of this element (A109, FIG. 4) and the 35S minimal promoter was used for transformation of *Arabidopsis* plants. Two to three weeks old seedlings and old leaves of the transformants were infiltrated with a 10 µM aqueous solution of the bacterial elicitor Flagellin 22 via a syringe (Felix, Plant Journal 18 (1999) 262-276; Gómez-Gómez, Plant Journal 18(1999) 277-284) which led to clear GUS activation. High induction was also observed after infection by a fungal (*Peronospora parasitica*) and a bacterial pathogen (*Pseudomonas syringae*).

*Peronospora* infections were carried out according to Dangl et al. (Genetic definition of loci involved in *Arabidopsis*-pathogen interactions. In: Methods in *Arabidopsis* Research (Koncz, Chua and Schell, eds.). Singapore: World Scientific Publishing Co. (1992), 393-418) or Koch (Plant Cell 2 (1990), 437-446).

On the other hand, mechanical stress induced for example by wounding did not activate the chimeric promoter. And surprisingly, no or only mere expression and activation of the reporter gene was observed in root which is the organ where the Eli17 gene is predominantly expressed in parsley. Thus, organ specificity appears not to be mediated by Box E17.

Furthermore, expression studies were performed the results of which are summarized in FIG. 8. Seven different tetramers of cis-elements were assayed for their background expression in aerial parts and roots, respectively, and for their inducibility after wounding, senescence, incompatible and compatible *Peronospora* infection. Some important conclusions can be drawn from these experiments:

All of these chimeric promoters that are inducible by incompatible strains of *Peronospora parasitica* are also inducible by compatible strains. This is an important observation regarding the present invention as it shows that these constructs could be inducible by all potential pathogens and not just those for which there is already a functional defense system in operation in the plant.

Although many constructs show induced expression around infection sites, the expression characteristics are different with, for example, some W Boxes (e.g. W2) being expressed in an area around the infection site whereas others are expressed within the infection site itself. This is an unexpected finding as it shows that within a class of cis-acting elements (W Boxes or GCC/S Boxes) differences in sequence outside of the core sequence lead to differences in functionality.

All of the cis-acting elements of the present invention show inducible expression in a heterologous plant (*Arabidopsis*). As these elements come from parsley, potato and wheat this clearly shows that these elements could be functional in all plants. This general functionality of such elements is an important new observation.

The invention also pertains to the following exemplary embodiments:

1. A chimeric promoter capable of mediating local gene expression in plants upon pathogen infection comprising (i) at least one cis-acting element sufficient to direct elicitor-specific expression comprising the nucleotide sequence of any one of SEQ ID NOS: 3 to 16, and (ii) a minimal promoter.

2. The chimeric promoter of embodiment 1, further comprising a cis-acting element having the nucleotide sequence of SEQ ID NO: 1 or 2.

3. The chimeric promoter of embodiment 1 or 2, wherein said synthetic plant promoter comprises homo- and/or heteromultimeric forms of said cis-acting element (s).

4. The chimeric promoter of any one of embodiments 1 to 3, wherein said multimeric form is a dimer or tetramer.

5. The chimeric promoter of any one of embodiments 1 to 4, wherein the minimal promoter is derived from the CaMV35S promoter, CHS promoter, PR1 promoter, or hcbt2 promoter.

6. The chimeric promoter of any one of embodiments 1 to 5, wherein the distance between said cis-acting element and said minimal promoter is 12 to 300 base pairs, more preferably 25 to 70 base pairs, and most preferably 40 to 60 base pairs.

7. The chimeric promoter of any one of embodiments 1 to 6, wherein a spacer region composed of 4 to 10 base pairs separates at least two of said cis-acting elements.

8. The chimeric promoter of any one of embodiments 3 to 7, wherein at least two of said multimeric forms are separated by a spacer of between about 50 to 1000 base pairs.

9. The chimeric promoter of any one of embodiments 1 to 8, wherein the induction of gene expression upon elicitor treatment or pathogen infection is at least 15-fold.

10. A recombinant gene comprising the chimeric promoter of any one of embodiments 1 to 9.

11. The recombinant gene of embodiment 10, wherein the chimeric promoter is operatively linked to a heterologous DNA sequence.

12. The recombinant gene of embodiment 10 or 11, wherein at least one of said cis-acting elements is located in the 5'- or 3-untranslated region or in an intron of the recombinant gene.

13. The recombinant gene of embodiment 11 or 12, wherein said heterologous DNA sequence encodes a (poly) peptide, cytotoxic protein, antibody, antisense RNA, sense RNA, ribozyme, transcription factor, protease, nuclease, lipase, or polymerase.

14. A vector comprising the chimeric promoter of any one of embodiments 1 to 9 or the recombinant gene of any one of embodiments 10 to 13.

15. A method for the production of transgenic plants, plant cells or plant tissue comprising the introduction of a chimeric promoter of any one of embodiments 1 to 9, a recombinant gene of any one of embodiments 10 to 13 or the vector of embodiment 14 into the genome of said plant, plant cell or plant tissue.

16. Plant cells comprising a chimeric promoter of any one of embodiments 1 to 9, the recombinant gene of any one of embodiments 10 to 13 or the vector of embodiment 14 or obtainable by the method of embodiment 15.

17. A transgenic plant or plant tissue comprising plant cells of embodiment 16.

18. The transgenic plant of embodiment 17, which upon the presence of the chimeric promoter or the recombinant gene attained resistance or improved resistance against a pathogen the corresponding wild-type plant was susceptible to.

19. Harvestable parts of a transgenic plant of embodiment 17 or 18 comprising plant cells of embodiment 16.

20. Propagation material of a transgenic plant of embodiment 17 or 18 comprising plant cells of embodiment 16.

21. A cis-acting element as defined in embodiment 1 or a multimeric form (s) of any one of those as defined in embodiment 3 or 4.

22. A method for the identification of an activator or inhibitor of genes specifically expressed in plants upon pathogen infection comprising the steps of: (a) providing a plant, plant cell, or plant tissue comprising a recombinant DNA molecule comprising a readout system operatively linked to the chimeric promoter of any one of embodiments 1 to 9; (b) culturing said plant cell or tissue or maintaining said plant in the presence of a compound or a sample comprising a plurality of compounds under conditions which permit expression of said readout system; (c) identifying or verifying a sample and compound, respectively, which leads to suppression or activation and/or enhancement of expression of said readout system in said plant, plant cell, or plant tissue.

23. The method of embodiment 22 further comprising the step of (d) subdividing the samples identified in step (c) and repeating steps (a) to (c) one or more times.

24. The method of embodiment 22 or 23 further comprising the step of (e) identifying and/or isolating from the identified sample the compound responsible for said suppression or activation and/or enhancement of expression of said readout system in said plant, plant cell, or plant tissue.

25. The method of any one of embodiments 22 to 24, wherein (a) said recombinant DNA molecule is a recombinant gene of any one of embodiments 10 to 13 or a vector of embodiment 14; (b) said plant cell is a plant cell of embodiment 16; (c) said plant tissue is a plant tissue of embodiment 17, or (d) said plant is a plant of embodiment 17 or 18.

26. A method for preparing a plant elicitor comprising the steps of the method of any one of embodiments 22 to 25 and formulating the compound obtained or identified in step (c) or (e) in a form suitable for the application in agriculture or plant cell and tissue culture.

27. A compound obtained or identified by the method of any one of embodiments 22 to 26 which is an activator or inhibitor of gene expression and/or function in plants.

28. An antibody specifically recognizing the compound of embodiment 27 or the cis-acting element of embodiment 21.

29. A diagnostic composition comprising a chimeric promoter of any one of embodiments 1 to 9, the recombinant gene of any one of embodiments 10 to 13, the vector of embodiment 14, the compound of embodiment 27 or the antibody of embodiment 28, and optionally suitable means for detection.

30. A kit comprising a chimeric promoter of any one of embodiments 1 to 9, the recombinant gene of any one of embodiments 10 to 13, the vector of embodiment 14, the compound of embodiment 27 or the antibody of embodiment 28.

31. A plant protection composition comprising the compound of embodiment 27.

32. Use of a cis-acting element sufficient to direct elicitor-specific expression, a chimeric promoter of any one of embodiments 1 to 9, the recombinant gene of any one of embodiments 10 to 13, the vector of embodiment 14, the cis-acting element of embodiment 21 and/or the compound of embodiment 27 for the production of pathogen resistant plants.

33. Use of a cis-acting element sufficient to direct elicitor-specific expression, the chimeric promoter of any one of embodiments 1 to 9, a recombinant gene of any one of embodiments 10 to 13, a vector of embodiment 14, the plant cell of embodiment 16, the plant tissue of embodiment 17, or the plant of embodiment 17 or 18 for identifying and/or producing compounds capable of conferring induced resistance to a pathogen in a plant.

34. A method of rendering a gene responsive to pathogens comprising inserting at least one cis-acting element sufficient to direct elicitor-specific expression into the promoter of said gene.

35. A method for preparing a promoter capable of mediating local gene expression in plants upon pathogen infection comprising operably linking a cis-acting element sufficient to direct elicitor-specific expression to a transcription initiation sequence of a promoter.

36. The method of embodiment 34 or 35, wherein said cis-acting element is a cis-acting element as defined in embodiment 1 or 2 or a multimeric form thereof as defined in any one of embodiments 3 to 8.

37. The method of any one of embodiments 34 to 36, further comprising deleting non-specific cis-acting elements in the promoter.

38. The promoter obtainable by the method of any one of embodiments 34 to 37.

39. Use of the compound of embodiment 27 as plant protective agent or herbicide.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A chimeric promoter capable of local gene expression in plants of an operably linked nucleic acid sequence, wherein the expression is induced by a pathogen elicitor treatment, a pathogen infection, or both wherein the promoter consists essentially of:
   (i) two cis-acting elements, wherein one of the two cis-acting elements consists of the nucleotide sequence of SEQ ID NO: 11, and
   (ii) a minimal promoter having a TATA box,
   wherein the distance between said two cis-acting elements of (i) and the TATA box of the minimal promoter of (ii) is between 25 and 70 base pairs.

2. The chimeric promoter of claim 1, wherein the two cis-acting elements of (i) are separated by a spacer of between about 4 to 10 base pairs.

3. A recombinant gene comprising the chimeric promoter of claim 1.

4. A vector comprising the chimeric promoter of claim 1.

5. A method for the production of a transgenic plant, a transgenic plant cell or a transgenic plant tissue, wherein the method comprises: introducing the chimeric promoter of claim 1 into the genome of a plant, a plant cell or a plant tissue to produce the transgenic plant, the transgenic plant cell or the transgenic plant tissue.

6. An isolated chimeric promoter to render a gene responsive to pathogens, obtained by a method comprising
   inserting at least one cis-acting element sufficient to direct pathogen-elicitor-induced expression, pathogen-infection induced expression, or both, of an operably linked nucleic acid, into the promoter of said gene, said promoter having a TATA box, wherein the at least one cis-acting element consists essentially of:
   two cis-acting elements, wherein one of the two cis-acting elements consists of the nucleotide sequence of SEQ ID NO: 11, and wherein the distance between said two cis-acting elements and the TATA box of said promoter is between 25 and 70 base pairs.

7. The chimeric promoter of claim 6, wherein the two cis-acting elements are separated by a spacer of between about 4 to 10 base pairs.

8. A recombinant gene wherein the isolated chimeric promoter of claim 6 is linked to a coding sequence for a gene.

9. A vector wherein the isolated chimeric promoter of claim 6 is linked to vector sequences.

10. A method for the production of a transgenic plant, a transgenic plant cell or a transgenic plant tissue, wherein the method comprises:
   introducing the isolated chimeric promoter of claim 6 into the genome of a plant, plant cell or plant tissue to produce the transgenic plant, the transgenic plant cell or the transgenic plant tissue.

* * * * *